US011406625B2

(12) United States Patent
Geva et al.

(10) Patent No.: US 11,406,625 B2
(45) Date of Patent: Aug. 9, 2022

(54) METHOD OF TREATING AMYOTROPHIC LATERAL SCLEROSIS WITH PRIDOPIDINE

(71) Applicant: PRILENIA NEUROTHERAPEUTICS LTD., Herzliya (IL)

(72) Inventors: Michal Geva, Even-Yehuda (IL); Ralph Laufer, Tel Aviv (IL); Michael Hayden, Herzliya (IL); Neta Zach, Tel Aviv (IL)

(73) Assignee: Prilenia Neurotherapeutics Ltd., Herzliya (IL)

( * ) Notice: Subject to any disclaimer, the term of this patent is extended or adjusted under 35 U.S.C. 154(b) by 30 days.

(21) Appl. No.: 16/789,564

(22) Filed: Feb. 13, 2020

(65) Prior Publication Data
US 2020/0179355 A1    Jun. 11, 2020

Related U.S. Application Data

(63) Continuation-in-part of application No. PCT/US2018/046481, filed on Aug. 13, 2018.

(60) Provisional application No. 62/545,315, filed on Aug. 14, 2017.

(51) Int. Cl.
| | | |
|---|---|---|
| *A61K 31/44* | (2006.01) | |
| *A61P 25/14* | (2006.01) | |
| *A61K 9/00* | (2006.01) | |
| *A61K 31/185* | (2006.01) | |
| *A61K 31/222* | (2006.01) | |
| *A61K 31/4152* | (2006.01) | |
| *A61K 31/426* | (2006.01) | |
| *A61K 31/4748* | (2006.01) | |
| *A61K 31/49* | (2006.01) | |

(52) U.S. Cl.
CPC ............ *A61K 31/44* (2013.01); *A61K 9/0053* (2013.01); *A61K 31/185* (2013.01); *A61K 31/222* (2013.01); *A61K 31/4152* (2013.01); *A61K 31/426* (2013.01); *A61K 31/4748* (2013.01); *A61K 31/49* (2013.01); *A61P 25/14* (2018.01)

(58) Field of Classification Search
CPC ..................................................... A61K 31/44
USPC ......................................................... 514/277
See application file for complete search history.

(56) References Cited

U.S. PATENT DOCUMENTS

| | | |
|---|---|---|
| 7,923,459 B2 | 4/2011 | Gauthier et al. |
| RE46,117 E | 8/2016 | Sonesson et al. |
| 2003/0139423 A1 | 7/2003 | Sonesson et al. |
| 2006/0135531 A1 | 6/2006 | Sonesson et al. |
| 2007/0238879 A1 | 10/2007 | Gauthier et al. |
| 2010/0105736 A1 | 4/2010 | Wikström |
| 2013/0150406 A1 | 6/2013 | Zimmermann et al. |
| 2013/0197031 A1 | 8/2013 | Sonesson |
| 2013/0267552 A1 | 10/2013 | Waters et al. |
| 2014/0315951 A1 | 10/2014 | Sonesson et al. |
| 2014/0378508 A1 | 12/2014 | Bassan et al. |
| 2015/0202302 A1 | 7/2015 | Lichet et al. |
| 2015/0209344 A1 | 7/2015 | Zimmermann et al. |
| 2015/0374677 A1 | 12/2015 | Schmidt et al. |
| 2016/0095847 A1 | 4/2016 | Sonesson |
| 2016/0166559 A1 | 6/2016 | Sonesson |
| 2016/0176821 A1 | 6/2016 | Wu et al. |
| 2016/0243098 A1 | 8/2016 | Geva et al. |
| 2017/0020854 A1 | 1/2017 | Licht et al. |
| 2017/0022158 A1 | 1/2017 | Barel et al. |

FOREIGN PATENT DOCUMENTS

| | | |
|---|---|---|
| WO | WO 2001/046145 A1 | 5/2001 |
| WO | WO 2003/101380 | 12/2003 |
| WO | WO 2006/040155 A1 | 4/2006 |
| WO | WO 2008/127188 A1 | 10/2008 |
| WO | WO 2008/133884 | 11/2008 |
| WO | WO 2012/0028635 A1 | 3/2012 |
| WO | WO 2013/034622 A1 | 3/2013 |
| WO | WO 2013/086425 A1 | 6/2013 |
| WO | WO 2013/152105 | 10/2013 |
| WO | WO 2014/052933 | 4/2014 |
| WO | WO 2014/181333 | 11/2014 |
| WO | WO 2014/205229 A1 | 12/2014 |
| WO | WO 2015/112601 A1 | 7/2015 |
| WO | WO 2016/003919 A1 | 1/2016 |
| WO | WO 2016/138130 A1 | 9/2016 |
| WO | WO 2016/138135 A1 | 9/2016 |
| WO | WO 2017/015609 A1 | 1/2017 |
| WO | WO 2017/015615 A1 | 1/2017 |
| WO | WO 2019/036358 | 2/2019 |

OTHER PUBLICATIONS

Banci et al. "SOD1 and amyotrophic lateral sclerosis: mutations and oligomerization" PloS one. Feb. 27, 2008;3(2):e1677.
Bilsland et al. "Deficits In axonal transport precede ALS symptoms in vivo" Proceedings of the National Academy of Sciences. Nov. 23, 2010;107(47):20523-8.
Bonni et al. "Cell survival promoted by the Ras-MAPK signaling pathway by transcription-dependent and-independent mechanisms" Science. Nov. 12, 1999;286(5443):1358-62.
Bozzoni et al. "Amyotrophic lateral sclerosis and environmental factors" Functional neurology. Jan. 2016;31(1):7.
Brod et al. "Combination therapy with glatiramer acetate (copolymer-1) and a type 1 interferon (IFN-α) does not improve experimental autoimmune encephalomyelitis" Annals of neurology. Jan. 2000;47(1):127-31.
Cedarbaum et al. "The ALSFRS-R: a revised ALS functional rating scale that incorporates assessments of respiratory function" Journal of the neurological sciences. Oct. 31, 1999;169(1-2):13-21.

(Continued)

*Primary Examiner* — Taofiq A Solola
(74) *Attorney, Agent, or Firm* — Mark S. Cohen; Pearl Cohen Zedek Latzer Baratz LLP

(57) ABSTRACT

Provided herein is a method for treating a human subject afflicted with ALS by administering to the subject a therapeutically effective amount of pridopidine as monotherapy or together with riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035) as combination or add-on therapy.

15 Claims, 12 Drawing Sheets

(56) References Cited

OTHER PUBLICATIONS

De Vos et al. "Neurobiology of axonal transport defects in motor neuron diseases: Opportunities for translational research?" Neurobiology of disease. Sep. 1, 2017;105:283-99.
De Vos et al. "Familial amyotrophic lateral sclerosis-linked SOD1 mutants perturb fast axonal transport to reduce axonal mitochondria content" Human molecular genetics. Nov. 15, 2007;16(22):2720-8.
Dextromethorphan hydrobromide/quinidine sulfate—Drug Summary, PDR (Prescribers' Digital Reference), http://www.pdr.net/drug-summary/Nuedexta-dextromethorphan-hydrobromide-quinidine-sulfate-1344.3281 accessed Aug. 14, 2017.
De Yebenes et al.. "Pridopidine for the treatment of motor function in patients with Huntington's disease (MermaiHD): a phase 3, randomised, double-blind, placebo-controlled trial" The Lancet Neurology. Dec. 1, 2011;10(12):1049-57.
Edaravone—Drug Summary, PDR (Prescribers' Digital Reference), www.pdr.net/drug-summary/Radicava-edaravone-24080 accessed Jul. 28, 2017.
Eykens et al. "The Genetic basis of amyotrophic lateral sclerosis: recent breakthroughs" Advances in Genomics and Genetics. Oct. 5, 2015;5:327-45.
Garcia-Miralles et al. "Early pridopidine treatment improves behavioral and transcriptional deficits in YAC128 Huntington disease mice" JCI insight. Dec. 7, 2017;2(23).
Geva et al. "Pridopidine activates neuroprotective pathways impaired in Huntington Disease" Human molecular genetics. Sep. 15, 2016;25(18):3975-87.
Guidance for Industry (In Vivo Drug Metabolism/Drug Interaction Studies—Study Design, Data Analysis, and Recommendations for Dosing and Labeling U.S. Department of Health and Human Services, Food and Drug Administration, Center for Drug Evaluation and Research (CDER) Center for Biologies Evaluation and Research (CBER) Nov. 1999.
Hammarström et al. "A fluorescent pentameric thiophene derivative detects in vitro-formed prefibrillar protein aggregates" Biochemistry. Aug. 17, 2010;49(32):6838-45.
Huntington Study Group HART Investigators. "A randomized, double-blind, placebo-controlled trial of pridopidine in Huntington's disease" Movement Disorders. Sep. 2013;28(10):1407-15.
International Search Report for PCT Application No. PCT/US2018/046481 dated Nov. 22, 2018.
Ionescu et al. "Compartmental microfluidic system for studying muscle-neuron communication and neuromuscular junction maintenance" European journal of cell biology. Feb. 1, 2016;95(2):69-88.
Langa et al. "Generation and phenotypic analysis of sigma receptor type I (σ1) knockout mice" European Journal of Neuroscience. Oct. 2003;18(8):2188-96.
Maier et al. "Differentiated NSC-34 motoneuron-like cells as experimental model for cholinergic neurodegeneration" Neurochemistry international. Jun. 1, 2013;62(8):1029-38.
Maurice et al. "Sigma-1 (σ 1) receptor in memory and neurodegenerative diseases" In Sigma Proteins: Evolution of the Concept of Sigma Receptors 2017 (pp. 81-108). Springer, Cham.
McGarry et al. "Safety and exploratory efficacy at 36 months in Open-HART, an open-label extension study of pridopidine in Huntington's disease" Journal of Huntington's disease. Jan. 1, 2017;6(3):189-99.
McGoldrick et al. "Rodent models of amyotrophic lateral sclerosis" Biochimica et Biophysica Acta (BBA)—Molecular Basis of Disease. Sep. 1, 2013;1832(9):1421-36.
Millecamps et al. "Axonal transport deficits and neurodegenerative diseases" Nature Reviews Neuroscience. Mar. 2013;14(3):161-76.
Perlson et al. "A switch in retrograde signaling from survival to stress in rapid-onset neurodegeneration" Journal of Neuroscience. Aug. 5, 2009;29(31):9903-17.
Peters et al. "Emerging mechanisms of molecular pathology in ALS" The Journal of clinical investigation. May 1, 2015;125(5):1767-79.

Petrov et al. "ALS clinical trials review: 20 years of failure. Are we any closer to registering a new treatment?" Frontiers in aging neuroscience. Mar. 22, 2017;9:68.
Picher-Martel et al. "From animal models to human disease: a genetic approach for personalized medicine in ALS" Acta neuropathologica communications. Dec. 1, 2016;4(1):70.
Ponten et al. "In vivo pharmacology of the dopaminergic stabilizer pridopidine" European journal of pharmacology. Oct. 10, 2010;644(1-3):88-95.
Rabinovich-Guilat et al. "The effect of mild and moderate renal impairment on the pharmacokinetics of pridopidine, a new drug for Huntington's disease" British journal of clinical pharmacology. Feb. 2016;81(2):246-55.
Rabinovich-Guilatt et al. "Metoprolol-pridopidine drug—drug interaction and food effect assessments of pridopidine, a new drug for treatment of Huntington's disease" British journal of clinical pharmacology. Oct. 2017;83(10):2214-24.
Riluzole—Drug Summary, PDR (Prescribers' Digital Reference), www.pdr.net/drug-summary/Rilutek-riluzole-526 accessed Jul. 28, 2017.
Riva et al. "Recent advances in amyotrophic lateral sclerosis" Journal of neurology. Jun. 1, 2016;263(6):1241-54.
Ryskamp et al. "The sigma-1 receptor mediates the beneficial effects of pridopidine in a mouse model of Huntington disease" Neurobiology of disease. Jan. 1, 2017;97:46-59.
Sahlholm et al. "The dopamine stabilizers ACR16 and (−)-OSU6162 display nanomolar affinities at the σ-1 receptor" Molecular psychiatry. Jan. 2013;18(1):12-4.
Sahlholm et al. "Pridopidine selectively occupies sigma-1 rather than dopamine D2 receptors at behaviorally active doses" Psychopharmacology. Sep. 1, 2015;232(18):3443-53.
Smith et al. "Enhanced bulbar function in amyotrophic lateral sclerosis: the Nuedexta treatment trial" Neurotherapeutics. Jul. 1, 2017;14(3):762-72.
Song MS, Matveychuk D, MacKenzie EM, Duchcherer M, Mousseau DD, Baker GB. An update on amine oxidase inhibitors: multifaceted drugs. Progress in neuro-psychopharmacology and biological psychiatry. Jul. 1, 2013;44:118-24.
Van Damme et al. "Modelling amyotrophic lateral sclerosis: progress and possibilities" Disease models & mechanisms. May 1, 2017;10(5):537-49.
Zahavi et al. "A compartmentalized microfluidic neuromuscular co-culture system reveals spatial aspects of GDNF functions" Journal of cell science. Mar. 15, 2015;128(6):1241-52.
Zou et al. "Toward precision medicine in amyotrophic lateral sclerosis" Annals of translational medicine. Jan. 2016;4(2).
Bender K: "How an innovative trial design may change the ALS treatment landscape"; NeurologyLive, retrieved from the Internet: URL: <https://www.neurologylive.com/view/howan-innovative-trial-design-may-change-the-als-treatment-landscape>. Feb. 26, 2020.
Bensimon, G., et al. A controlled trial of riluzole in amyotrophic lateral sclerosis. *New Engiand Journal of Medicine*, 1994, 330.9: 585-591.
Bigica A: The road to success in ALS: Details of the AMX0035 CENTAUR trial; NeurologyLive, retrieved from the Internet: URL: <https://www.neurologylive.com/view/theroad-to-success-in-als-details-of-the-amx0035-centaur-triab, Dec. 19, 2019.
Como, Peter G., et al. A controlled trial of fluoxetine in nondepressed patients with Huntington's disease. *Movement disorders: official journal of ths Movement Disorder Society*, 1997, 12.3: 397-401.
Cudkowicz, Merit, et al. The effects of dexpramipexole (KNS-760704) in individuals with amyotrophic lateral sclerosis. *Nature medicine*, 2011, 17.12: 1652-1656.
Figueiredo M: "FDA gives OK to HEALEY ALS platform trial testing zilucoplan, CNMAu8, and verdiperstat"; ALS News Today, retrieved from the internet: URL: <https://alsnewstoday.com/news-posts/2020/01/27/fda-gives-ok-healey-als-platform-trial-testing-firstthree-therapies-zilucoplan-cnm-au8-verdiperstat/>. Jan. 27, 2020.
International Search Report for PCT/IL2021/050172 dated Apr. 19, 2021.
Ionescu A et al.: "Targeting the Sigma-1 receptor via pridopidine ameliorates central features of ALS pathology in a SOD1G93A

(56) References Cited

OTHER PUBLICATIONS model"; Cell Death Dis, vol. 10, No. 3, p. 210 (1-19), DOI: 10.1038/s41419-019-1451-2 Mar. 1, 2019 (Mar. 1, 2019) The whole document.

Nagase, Midori, et al. Increased oxidative stress in patients with amyotrophic lateral sclerosis and the effect of edaravone administration. *Redox Report*, 2016, 21.3: 104-112.

Beglinger, Leigh J., et al. Results of the citalopram to enhance cognition in Huntington disease trial. *Movement Disorders*, 2014, 29.3: 401-405.

Bensimon, G., et al. A controlled trial of riluzole in amyotrophic lateral sclerosis. *New England Journal of Medicine*, 1994, 330.9: 585-591.

Como, Peter G., et al. A controlled trial of fluoxetine in nondepressed patients with Huntington's disease. *Movement disorders: official journal of the Movement Disorder Society*, 1997, 12.3: 397-401.

Cubo, E., et al. Effect of donepezil on motor and cognitive function in Huntington disease. *Neurology*, 2006, 67.7: 1268-1271.

Koschnitzky, Jenna E., et al. Effect of fluoxetine on disease progression in a mouse model of ALS. *Journal of neurophysiology*, 2014, 111.11: 2164-2176.

Landwehrmeyer, G. Bernhard, et al. Riluzole in Huntington's disease: a 3-year, randomized controlled study. *Annals of Neurology: Official Journal of the American Neurological Association and the Child Neurology Society*, 2007, 62.3: 262-272.

Miller, R. G., et al. (2012). Riluzole for amyotrophic lateral sclerosis (ALS)/motor neuron disease (MND). Cochrane database of systematic reviews, (3).

Mowla, A., et al. (2007). Does fluoxetine have any effect on the cognition of patients with mild cognitive impairment?: a double-blind, placebo-controlled, clinical trial. Journal of clinical psychopharmacology, 27(1), 67-70.

Rampello, L., et al. (2002). The SSRI, citalopram, improves bradykinesia in patients with Parkinson's disease treated with L-dopa. Clinical neuropharmacology, 25(1), 21-24.

Sawada, H. (2017). Clinical efficacy of edaravone for the treatment of amyotrophic lateral sclerosis. Expert opinion on pharmacotherapy, 18(7), 735-738.

Smith, R., et al. (2017). Enhanced bulbar function in amyotrophic lateral sclerosis: the Nuedexta treatment trial. Neurotherapeutics, 14(3), 762-772.

Walker, F. O., & Hunt, V. P. (1989). An open label trial of dextromethorphan in Huntington's disease. Clinical neuropharmacology, 12(4), 322-330.

← Retrograde

METHOD OF TREATING AMYOTROPHIC LATERAL SCLEROSIS WITH PRIDOPIDINE

CROSS REFERENCE TO RELATED APPLICATIONS

This application is a Continuation-in-Part Application from International Patent Application No. PCT/US2018/046481 filed Aug. 13, 2018, which claims the benefit of U.S. Provisional Application No. 62/545,315, filed Aug. 14, 2017 the entire content of which are hereby incorporated by reference herein.

BACKGROUND OF THE INVENTION

Amyotrophic Lateral Sclerosis

Amyotrophic lateral sclerosis (ALS) is a devastating degenerative disease characterized by progressive loss of motor neurons in the motor cortex, brainstem, and spinal cord (Peters 2015). This rapidly progressing fatal disease leads to weakness of limb, respiratory, and bulbar muscles. Patients progressively lose control of voluntary muscles, leading to loss of limb function and the ability to chew, swallow, speak and eventually breathe.

ALS is a rare condition, having a mean incidence rate of 2.8/100,000 in Europe and 1.8/100,000 in North America, and a mean prevalence rate of 5.40/100,000 in Europe and 3.40/100,000 in North America (Bozzoni 2016).

About 10% of ALS cases are classified as familial (fALS), whereas the remaining 90% are classified as sporadic (sALS) and occur randomly (Riva 2016). Over 60% of patients die within 3 years of presentation, usually from respiratory failure and about 10% survive for more than 10 years (Zou 2016). There is no currently known disease-modifying therapy in the art for ALS, although riluzole slows the rate of progression of the disease and prolongs survival by 2 or 3 months and edaravone slows physical decline (Jaiswal 2018).

Clinical manifestations of ALS include muscle weakness and hypotrophy, fasciculations and cramps, spastic hypertonus, and hyperreflexia are the main clinical manifestations. Some patients also display dysarthria, dysphagia and respiratory weakness. Non-motor symptoms include behavioral disturbances, dysexecutive impairment, and frontotemporal dementia.

The neuropathological features of ALS include muscle atrophy, loss of anterior horn cells, and sclerosis of the spinal cord lateral columns (Martel 2016). Gliosis, defined as activation of astrocytes and microglia, is also a hallmark of ALS.

Pridopidine

Pridopidine (formerly ACR16, Huntexil®) is a unique compound developed for the treatment of patients with Huntington's disease. The chemical name of pridopidine is 4-(3-(Methylsulfonyl)phenyl)-1-propylpiperidine, and its Chemical Registry Number is CAS 346688-38-8 (CSID: 7971505, 2016). The Chemical Registry number of pridopidine hydrochloride is 882737-42-0 (CSID:25948790 2016). Processes of synthesis of pridopidine and a pharmaceutically acceptable salt thereof are disclosed in U.S. Pat. No. 7,923,459 and PCT Application Publication No. WO 2017/015609. U.S. Pat. No. RE46,117 discloses pridopidine for the treatment of a variety of diseases and disorders.

Pridopidine has been shown to modulate motor activity by either suppressing hyperactivity or enhancing hypoactivity. Pridopidine also demonstrates neuroprotective properties, which are suggested to be attributed to its high affinity to the sigma-1 receptor (S1R, binding IC50~70-80 nM) (Sahlholm 2013), while the motor activity of pridopidine was suggested to be mediated primarily by its low-affinity, antagonistic activity at the dopamine D2 receptor (D2R) (binding IC50~10 µM) (Ponten 2010, Sahlholm 2015). Pridopidine shows low-moderate affinity binding to additional receptors in the micromolar range.

The S1R is an endoplasmic reticulum (ER) chaperone protein implicated in cellular differentiation, neuroplasticity, neuroprotection and cognitive function in the brain. Recently, transcriptomic analysis of rat striatum showed that pridopidine treatment activates expression of the BDNF, dopamine receptor 1 (D1R), glucocorticoid receptor (GR), and the serine-threonine kinase protein kinase B (Akt)/phosphoinositide 3-kinase (PI3K) pathways. Pridopidine was shown to enhance secretion of the neuroprotective brain-derived neurotrophic factor (BDNF) in a neuroblastoma cell line, in a S1R-dependent manner (Geva 2016) and to rescue spine impairment and aberrant calcium signaling by activation of the S1R (Ryskamp 2017).

PCT International Patent Application Publication No. WO2016/138135 discloses use of S1R agonists to treat, inter alia, familial adult amyotrophic lateral sclerosis (ALS) and juvenile amyotrophic lateral sclerosis (ALS).

There remains an unmet need to provide effective treatments for ALS, in particular sporadic ALS.

SUMMARY OF THE INVENTION

The present invention is based, at least in part, on the surprising experimental discovery that pridopidine treatment improves axonal transport deficits, enhances ERK activation and restores neuromuscular junction (NMJ) activity in SOD1 impaired muscle cell co-cultures, reduces mutant SOD1 aggregates in the spinal cord, and attenuates NMJ disruption and subsequent muscle wasting in SOD1 impaired mice.

The invention provides for a method for treating a subject afflicted with amyotrophic lateral sclerosis (ALS), comprising periodically administering to the subject an amount of pridopidine effective to treat the human subject.

The invention also provides for pridopidine for use in treating a human subject afflicted with ALS.

The invention also provides a method for treatment of ALS comprising periodically administering to a subject in need thereof an amount of pridopidine effective to treat the ALS.

In some embodiments the subject is afflicted with sporadic ALS.

The invention also provides for a pharmaceutical composition for treating a human subject afflicted with ALS comprising an effective amount of pridopidine.

The invention also provides for the use of pridopidine in the manufacture of a medicament for the treatment of ALS.

Further provided is a package comprising pridopidine and optionally instructions for using the pridopidine to treat ALS.

In one embodiment, pridopidine is administered as a monotherapy to a subject afflicted with ALS. In other embodiments, a subject afflicted with ALS is treated with pridopidine and with one or more additional agents.

Further provided is a method of treating a subject afflicted with ALS comprising periodically administering to the subject an amount of riluzole, and an amount of pridopidine.

Further provided is a method of treating a subject afflicted with ALS comprising periodically administering to the subject an amount of edaravone, and an amount of pridopidine.

Further provided is a method of treating a subject afflicted with ALS comprising periodically administering to the subject an amount of dextromethorphan/quinidine and an amount of pridopidine.

Further provided is a method of treating a subject afflicted with ALS comprising administering to the subject an amount of sodium phenylbutyrate (PB) or tauroursodeoxycholic acid (TUDCA) and an amount of pridopidine.

Further provided is a method of treating a subject afflicted with ALS comprising administering to the subject an amount of combination of sodium phenylbutyrate (PB) and tauroursodeoxycholic acid (i.e. AMX0035) and an amount of pridopidine.

Further provided is a package comprising:
a) a first pharmaceutical composition comprising an amount of an agent which is riluzole, edaravone, combination of dextromethorphan/quinidine, sodium phenylbutyrate (PB), tauroursodeoxycholic acid or a combination of sodium phenylbutyrate (PB)/tauroursodcoxycholic acid (i.e. AMX0035); and
b) a second pharmaceutical composition comprising and amount of pridopidine and a pharmaceutically acceptable carrier.

In a further embodiment, the package also comprises:
c) instructions for use for the first and the second pharmaceutical compositions together to treat a subject afflicted with ALS.

In some embodiments, the first pharmaceutical composition is riluzole, edaravone, a combination of dextromethorphan/quinidine, laquinimod, sodium phenylbutyrate (PB), tauroursodeoxycholic acid or a combination of sodium phenylbutyrate (PB)/tauroursodeoxycholic acid (i.e. AMX0035).

Further provided is pridopidine for use as an add-on therapy of or in combination with riluzole in treating a subject afflicted with ALS. Further provided is pridopidine for use as an add-on therapy of or in combination with edaravone in treating a subject afflicted with ALS. Further provided is pridopidine for use as an add-on therapy of or in combination with dextromethorphan/quinidine in treating a subject afflicted with ALS. Further provided is pridopidine for use as an add-on therapy of or in combination with sodium phenylbutyrate (PB) in treating a subject afflicted with ALS. Further provided is pridopidine for use as an add-on therapy of or in combination with tauroursodeoxycholic acid in treating a subject afflicted with ALS. Further provided is pridopidine for use as an add-on therapy of or in combination with a combination of sodium phenylbut-rate (PB)/tauroursodeoxycholic acid (i.e. AMX0035) in treating a subject afflicted with ALS.

The subject invention also provides a pharmaceutical composition comprising an amount of riluzole, edaravone combination of dextromethorphan/quinidine, sodium phenylbutyrate (PB), tauroursodeoxycholic acid or a combination of sodium phenylbutyrate (PB)/tauroursodeoxycholic acid (i.e. AMX0035) and an amount of pridopidine, and at least one pharmaceutical acceptable carrier.

The subject invention also provides the use of:
a) an amount of riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035); and
b) an amount of pridopidine
in the preparation of a combination for treating a subject afflicted with ALS wherein the amount of riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035) and the amount of pridopidine are administered simultaneously or contemporaneously.

The subject invention also provides a pharmaceutical composition comprising an amount of riluzole, edaravone, dextromethorphan/quinidine or sodium phenylbutyrate (PB), tauroursodeoxycholic acid or sodium phenylbutyrate (PB)/tauroursodeoxycholic acid (i.e. AMX0035) for use in treating a subject afflicted with a movement disorder, in combination with an amount of pridopidine, by periodically administering to the subject the pharmaceutical composition and the amount of pridopidine.

The subject invention also provides a pharmaceutical composition comprising an amount of pridopidine for use treating a subject afflicted with a movement disorder, in combination with an amount of riluzole, edaravone, dextromethorphan/quinidine, sodium phenylbutyrate (PB), tauroursodeoxycholic acid or sodium phenylbutyrate (PB)/tauroursodeoxycholic acid (i.e. AMX0035), by periodically administering to the subject the pharmaceutical composition and the amount of riluzole, edaravone, dextromethorphan/quinidine, sodium phenylbutyrate (PB), tauroursodeoxycholic acid or sodium phenylbutyrate (PB)/tauroursodeoxycholic acid (i.e. AMX0035), respectively.

The subject invention also provides riluzole and pridopidine for the treatment of a subject afflicted with a movement disorder, wherein the riluzole and the pridopidine are administered simultaneously, or contemporaneously.

The subject invention also provides a product containing an amount of riluzole and an amount of pridopidine for simultaneous or contemporaneous use in treating a subject afflicted with ALS.

In another aspect, the invention provides a combination of pridopidine, and riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035), for use as a medicament for the treatment, prevention or alleviation of ALS.

In another aspect the invention provides a combination of pridopidine, and riluzole, edaravone, laquinimod, combination of dextromethorphan/quinidine, sodium phenylbutyrate (PB), tauroursodeoxycholic acid or combination of sodium phenylbutyrate (PB)/tauroursodeoxycholic acid (i.e. AMX0035), for use as a medicament.

In another aspect the invention provides a pharmaceutical composition comprising a therapeutically effective amount of pridopidine, and a therapeutically effective amount of riluzole, edaravone, laquinimod, combination of dextromethorphan/quinidine, sodium phenylbutyrate (PB), tauroursodeoxycholic acid or combination of sodium phenylbutyrate (PB)/tauroursodeoxycholic acid (i.e. AMX0035), together with one or more adjuvants, excipients, carriers and/or diluents.

In another aspect the invention provides a method of treating of ALS in a living animal body, including a human, which method comprises the step of administering to such a living animal body in need thereof, a therapeutically effective amount of pridopidine; in a combination therapy with riluzole, edaravone, laquinimod, combination of dextromethorphan/quinidine, sodium phenylbutyrate (PB), tauroursodcoxycholic acid or combination of sodium phenylbutyrate (PB)/tauroursodcoxycholic acid (i.e. AMX0035).

In another aspect the invention provides a kit of parts comprising at least two separate unit dosage forms (A) and (B), wherein (A) comprises pridopidine; and (B) comprises riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035); and optionally (C) instructions for the simultaneous or contemporaneous administration of the pridopidine of (A) and the riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035) of (B), to a patient in need thereof.

In another aspect the invention provides a method of treating a subject afflicted with ALS comprising administering to the subject a combination of a therapeutically effective amount of pridopidine, and a therapeutically effective amount of riluzole, edaravone, laquinimod, combination of dextromethorphan/quinidine, sodium phenylbutyrate (PB), tauroursodeoxycholic acid or combination of sodium phenylbutyrate (PB)/tauroursodeoxycholic acid (i.e. AMX0035), wherein the amounts when taken together are effective to treat the human patient.

BRIEF DESCRIPTION OF THE FIGURES

FIG. 1a. Experimental workflow for the axonal transport assay. FIG. 1b. Schematic illustration of the experimental system for axonal transport tracking in motor neurons (MNs). FIG. 1c. Time lapse images of Qdot-BDNF (bright orange) axonal transport.

FIG. 2b. Pridopidine's effect on particle stop count (number of counted stops of Qdot-BDNF per second).

FIG. 5b. Muscle contraction traces as extracted from intensity over time measurements of muscle contraction.

FIG. 7a. Percent of contracting myoblasts in co-cultures of ventral spinal cord (WT or SOD1 G93A) sections and primary myocytes (SOD1G93A or LM controls). FIG. 7b. Pridopidine's effect on neuromuscular junction (NMJ) in muscle tissue from WT or SOD1G93A and motor neurons from WT or S1R−/− mice.

FIG. 8a. Pridopidine's effect on total ERK (tERK) and phosphorylated ERK (pERK) levels shown in Western blots from WT, SOD1G93A, and S1R−/− MNs culture extracts. FIG. 8b. Quantification of pridopidine's effect of ERK activation as measured by tERK/pERK.

FIG. 9a. Visualization and quantification of fluorescently labeled spinal cords with NC500 to label mutant SOD1 aggregates in WT and SOD1G93A spinal cords, treated or not with pridopidine. FIG. 9b Quantitative analysis of the number of aggregates per area identified in the gray matter. FIG. 9c Quantitative analysis of the number of aggregates per area identified in the white matter.

FIG. 10a. Representative images of H&E-stained cross sections from Gastrocnemius muscle of WT or SOD1G93A mice treated or not with Pridopidine. FIG. 10b. Assessment of pridopidine's effect on muscle fiber wasting: quantitative analysis of pridopidine's effect on muscle fiber diameter.

FIG. 11a. Pridopidine's effect NMJ preservation in vivo. FIG. 11b. Quantitative analysis of pridopidine's effect on the percentage of innervated NMJs.

DETAILED DESCRIPTION OF THE INVENTION

Figure 1A:
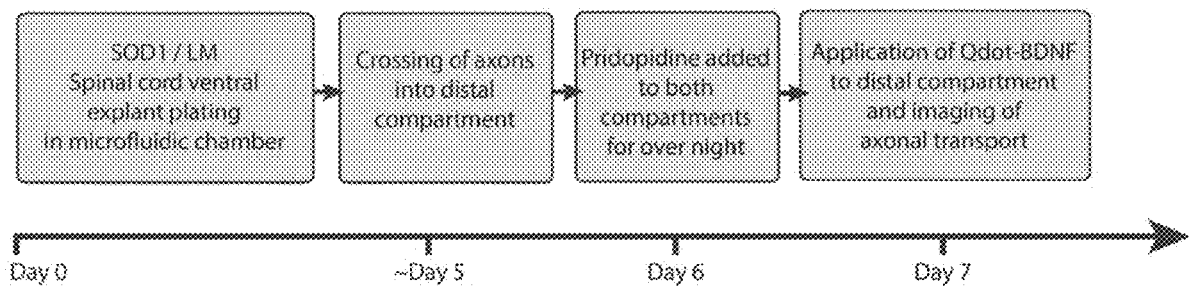
FIGS. 1a-1c. Axonal transport assay.

The invention provides for a method for treating a subject afflicted with amyotrophic lateral sclerosis (ALS), comprising periodically administering to the subject an amount of pridopidine effective to treat the human subject.

In an embodiment of the invention, the ALS is sporadic ALS.

In an embodiment of the invention, the ALS is familial ALS (FALS). In some embodiments the ALS is juvenile ALS (JALS).

In some embodiments the ALS is not FALS. In some embodiments the ALS is not juvenile ALS (JALS).

In an embodiment of the invention, the type of ALS is classic, bulbar, flail arm, flail leg, pyramidal and respiratory ALS, progressive muscular atrophy, primary lateral sclerosis or progressive bulbar palsy.

In an embodiment of the invention, the subject carries a mutant version of a gene that causes or contributes to ALS pathogenesis. In some embodiments the mutant version of the gene is selected from the group of genes consisting of the superoxide dismutase 1 (SOD1), TAR DNA-binding protein (TARDBP) encoding TDP-43, fused in sarcoma (FUS), p62 (SQSTM1), ubiliquin-2 (UBQLN2). TANK-binding kinase 1 (TBK 1), profilin 1 (PFN1), VCP or p97 (VCP), angiogenin (ANG), optineurin (OPTN), C9orf72, Sigma-1 Receptor (S1R), Tubulin alpha-4A (TUBA4A), Dynactin (DCTN1), hnRNPA1 (HNRNPA1), Matrin 3 (MATR3), Coiled-coil-helix-coiled-coil-helix domain containing 10 (CHCHD10) genes and any combination thereof.

In an embodiment of the invention, the amount of pridopidine is effective to inhibit or reduce progression of a symptom of the ALS in the subject.

In an embodiment of the invention, the symptom of ALS is a clinical symptom of ALS.

In an embodiment of the invention, the symptom of ALS is muscle weakness and hypotrophy, fasciculations and cramps, spastic hypertonus, hyperreflexia, dysarthria, dysphagia and respiratory weakness, behavioral disturbances, dysexecutive impairment, or frontotemporal dementia.

In an embodiment of the invention, the symptom of ALS is a neuropathological symptom.

In some embodiments, the symptom is bulbar palsy or pseudobulbar affect (PBA).

In an embodiment of the invention, the symptom of ALS is muscle atrophy, loss of motor neurons, loss of anterior horn cells, sclerosis of the spinal cord lateral columns, or gliosis.

In one embodiment, the symptom of ALS is a rate of decline (a) in pulmonary function, (b) in functional disability, or (c) in the ability score for the lower extremities. In an embodiment of the invention, the amount of pridopidine is effective to cause survival of the subject or cause neuroprotection in the subject.

In some embodiments of the invention, treatment of the subject with pridopidine results in a lessened decline or an improvement in the subject, in one or more of the following domains,
1) speech, 2) salivation, 3) swallowing, 4) handwriting, 5) cutting food and handling utensils (with or without gastrostomy), 6) dressing and hygiene, 7) turning in bed and adjusting bed clothes, 8) walking, 9) climbing stairs, 10) breathing, 11) dyspnea, 12) orthopnea, and 13) insufficiency.

In some embodiments, patients are monitored for changes in the above domains using a rating scale, for example the Amyotrophic Lateral Sclerosis Functional Rating Scale (ALSFRS) or revised ALSFRS (ALSFRS-R) and a functional change in a patient is monitored over time.

In some embodiments, pseudobulbar affect (PBA) (as measured by CNS-LS) is monitored in the patients. In some embodiments, the severity and/or frequency of emotional outbursts in subjects experiencing PBA is reduced with pridopidine treatment.

In some embodiments of the invention, use of pridopidine maintains, improves or lessens the decline of in disease severity as measured by the ALS Functional Rating Scale-Revised (ALSFRS-R) in ALS patients and/or ALSAQ-5.

In some embodiments of the invention, use of pridopidine maintains, improves or lessens the decline in respiratory function as assessed by slow vital capacity (SVC) in ALS patients.

In some embodiments of the invention, use of pridopidine maintains, improves or lessens the decline in muscle strength as measured by hand held dynamometry (HHD) in ALS patients.

In some embodiments of the invention, use of pridopidine results in maintenance, reduction or less increase in phosphorylated neurofilament heavy chain (pNfH) and neurofilament light chain (NfL) in plasma and CSF in ALS patients.

In some embodiments of the invention, use of pridopidine results in maintenance, reduction or less increase in urinary neurotrophin receptor p75 extracellular domain ($p75^{ECD}$) in ALS patients.

In some embodiments of the invention, use of pridopidine maintains, improves or lessens the decline in speech characteristics as measured by the slope of change in the CNS-BFS speech subdomain in ALS patients.

In some embodiments of the invention, use of pridopidine in ALS patients maintains, improves or lessens the decline in voice characteristics as determined by Aural Analytics set of analyses in ALS patients.

In some embodiments of the invention, use of pridopidine maintains, improves or lessens the decline in cognitive function as measured by the Edinburgh Cognitive and Behavioral ALS Screen (ECAS) in ALS patients.

In some embodiments of the invention, use of pridopidine maintains, improves or lessens the decline in home-based clinical assessments (weekly ALSFRS-R, SVC, pinch strength) in ALS patients.

In some embodiment, use of pridopidine maintains, improves or lessens the decline in bulbar function as measured by the CNS-BFS (Center for Neurologic Study Bulbar Function Scale) and the bulbar subdomain (Q1-Q3) score of the ALSFRS-R total score in ALS patients.

In some embodiment, use of pridopidine maintains, improves or lessens the decline in muscle strength, as measured isometrically using hand-held dynamometry (HHD) and grip strength in ALS patients.

In some embodiment, use of pridopidine maintains, improves or lessens the decline in bulbar function as measured by the slope of change in the CNS-BFS total score in ALS patients.

In some embodiment, use of pridopidine maintains, improves or lessens the decline in bulbar function as measured by the slope of change in the CNS-BFS total score in ALS patients whose calculated ALSFRS-R slope at baseline (48-ALSFRS-R total score at baseline/time since onset) is equal to or greater than 0.75 pt/month.

In some embodiment, use of pridopidine reduces the percentage of ALS patients who develop bulbar symptoms by 6 months among participants without bulbar symptoms at baseline (as defined as a CNS-BFS score<30 at baseline) in the active compared to placebo groups.

In an embodiment of the invention, pridopidine is administered daily.

In an embodiment of the invention, pridopidine is administered more often than once daily.

In an embodiment of the invention, pridopidine is administered twice daily. In an embodiment of the invention, pridopidine is administered thrice daily.

In an embodiment of the invention, pridopidine is administered less often than once daily, for example, on alternate days, three times per week, twice per week or once per week.

In an embodiment of the invention, pridopidine is administered daily, twice a week, three times a week or more often than once daily.

In an embodiment of the invention, pridopidine is administered orally.

In some embodiments, a unit dose of the pharmaceutical composition contains 10-250 mg pridopidine. In some embodiments the composition comprises 45 mg, 67.5 mg, 90 mg, or 112.5 mg of pridopidine.

In an embodiment, between 10-225 mg pridopidine is administered to the patient per day. In another embodiment, between 45-180 mg pridopidine is administered to the patient per day. In another embodiment, 10 mg, 22.5 mg, 45 mg, 67.5, mg, 90 mg, 100 mg, 112.5 mg, 125 mg, 135 mg, 150 mg, or 180 mg pridopidine is administered to the patient per day.

In an embodiment, the pharmaceutical composition is administered twice per day. In another embodiment, an equal amount of the pharmaceutical composition is administered at each administration. In an embodiment, the two doses are administered at least 6 hours apart, at least 7 hours, at least 8 hours, at least 9 hours, at least 10 hours, at least 11 hours apart. In some embodiments, the pharmaceutical composition is administered for at least 12 weeks, at least 20 weeks, at least 24 weeks, at least 26 weeks, at least 52 weeks, or at least 78 weeks.

In an embodiment of the invention, the pridopidine is pridopidine hydrochloride.

In an embodiment of the invention, the subject is a human subject.

The invention also provides for pridopidine for use in treating a human subject afflicted with ALS.

The invention also provides for a pharmaceutical composition for use in treating a human subject afflicted with ALS comprising an effective amount of pridopidine.

The invention further provides a method for the treatment of ALS comprises periodically administering to a subject in need thereof an amount of pridopidine effective to treat the ALS.

In an embodiment, the pharmaceutical composition comprises an amount of pridopidine and an amount of a second compound, for example a compound useful in treating patients with ALS.

In some embodiments, the second compound is riluzole, edaravone, a combination of dextromethorphan and quinidine, laquinimod, sodium phenylbutyrate (PB), tauroursodeoxycholic acid or combination of sodium phenylbutyrate (PB) and tauroursodeoxycholic acid (i.e. AMX0035).

In an embodiment, the pharmaceutical composition for use in treating a subject afflicted with ALS, comprises pridopidine and a second compound which are prepared to be administered simultaneously or contemporaneously.

In an embodiment, the pharmaceutical composition is in a unit dosage form, useful in treating subject afflicted with ALS, which comprises:
a) an amount of pridopidine;
b) an amount of second compound,
wherein the respective amounts of said second compound and said pridopidine in said composition are effective, upon concomitant administration to said subject of one or more of said unit dosage forms of said composition, to treat the subject. In some embodiments, the second compound is riluzole, edaravone, combination of dextromethorphan/quinidine, sodium phenylbutyrate (PB), tauroursodeoxycholic acid or combination of sodium phenylbutyrate (PB)/tauroursodeoxycholic acid (i.e. AMX0035).

In an embodiment, the pharmaceutical composition comprises an amount of pridopidine for use in treating a subject afflicted with ALS as an add-on therapy to a second compound which is riluzole. In another embodiment, the pharmaceutical composition comprises an amount of pridopidine for use in treating a subject afflicted with ALS as an add-on therapy to a second compound which is edaravone. In another embodiment, the pharmaceutical composition comprises an amount of pridopidine for use in treating a subject afflicted with ALS as an add-on therapy to a second compound which is dextromethorphan/quinidine. In another embodiment, the pharmaceutical composition comprises an amount of pridopidine for use in treating a subject afflicted with ALS as an add-on therapy to a second compound sodium phenylbutyrate (PB). In another embodiment, the pharmaceutical composition comprises an amount of pridopidine for use in treating a subject afflicted with ALS as an add-on therapy to a second compound tauroursodeoxycholic acid. In another embodiment, the pharmaceutical composition comprises an amount of pridopidine for use in treating a subject afflicted with ALS as an add-on therapy to combination of sodium phenylbutyrate (PB) and tauroursodeoxycholic acid (i.e. AMX0035).

In an embodiment, the pharmaceutical composition comprises an amount of pridopidine for use in treating a subject afflicted with ALS simultaneously or contemporaneously with a second compound which is riluzole. In another embodiment, the pharmaceutical composition comprises an amount of pridopidine for use in treating a subject afflicted with ALS simultaneously or contemporaneously with a second compound which is edaravone. In another embodiment, the pharmaceutical composition comprises an amount of pridopidine for use in treating a subject afflicted with ALS simultaneously or contemporaneously with a second compound which is dextromethorphan/quinidine. In another embodiment, the pharmaceutical composition comprises an amount of pridopidine for use in treating a subject afflicted with ALS simultaneously or contemporaneously with a second compound which is laquinimod. In another embodiment, the pharmaceutical composition comprises an amount of pridopidine for use in treating a subject afflicted with ALS simultaneously or contemporaneously with a second compound which is sodium phenylbutyrate (PB). In another embodiment, the pharmaceutical composition comprises an amount of pridopidine for use in treating a subject afflicted with ALS simultaneously or contemporaneously with a second compound which is tauroursodeoxycholic acid. In another embodiment, the pharmaceutical composition comprises an amount of pridopidine for use in treating a subject afflicted with ALS simultaneously or contemporaneously with a combination of sodium phenylbutyrate (PB) and tauroursodeoxycholic acid (i.e. AMX0035). In an embodiment, the pharmaceutical composition comprises an amount of a compound which is riluzole for use in treating a subject afflicted with ALS as an add-on therapy to pridopidine. In another embodiment, the pharmaceutical composition comprises an amount of a compound which is edaravone for use in treating a subject afflicted with ALS as an add-on therapy to pridopidine. In another embodiment, the pharmaceutical composition comprises an amount of a compound which is dextromethorphan/quinidine for use in treating a subject afflicted with ALS as an add-on therapy to pridopidine. In another embodiment, the pharmaceutical composition comprises an amount of a compound which is laquinimod for use in treating a subject afflicted with ALS as an add-on therapy to pridopidine. In another embodiment, the pharmaceutical composition comprises an amount of a compound which is sodium phenylbutyrate (PB) for use in treating a subject afflicted with ALS as an add-on therapy to pridopidine. In another embodiment, the pharmaceutical composition comprises an amount of a compound which is tauroursodeoxycholic acid for use in treating a subject afflicted with ALS as an add-on therapy to pridopidine. In another embodiment, the pharmaceutical composition comprises an amount of a combination of sodium phenylbutyrate (PB) and tauroursodeoxycholic acid for use in treating a subject afflicted with ALS as an add-on therapy to pridopidine. In an embodiment, the pharmaceutical composition comprises an amount of a compound which is riluzole for use in treating a subject afflicted with ALS simultaneously or contemporaneously with pridopidine. In another embodiment the pharmaceutical composition comprises an amount of a compound which is edaravone for use in treating a subject afflicted with ALS simultaneously or contemporaneously with pridopidine. In another embodiment the pharmaceutical composition comprises an amount of a compound which is dextromethorphan/quinidine for use in treating a subject afflicted with ALS simultaneously or contemporaneously with pridopidine. In another embodiment the pharmaceutical composition comprises an amount of a compound which is sodium phenylbutyrate (PB) for use in treating a subject afflicted with ALS simultaneously or contemporaneously with pridopidine. In another embodiment the pharmaceutical composition comprises an amount of a compound which is tauroursodeoxycholic acid for use in treating a subject afflicted with ALS simultaneously or contemporaneously with pridopidine. In another embodiment the pharmaceutical composition comprises an amount of combination of sodium phenylbutyrate (PB)/tauroursodeoxycholic acid (i.e. AMX0035) for use in treating a subject afflicted with ALS simultaneously or contemporaneously with pridopidine.

The invention also provides for a compound which is riluzole for use as an add-on therapy to pridopidine in treating a subject afflicted with ALS.

The invention also provides for a compound which is edaravone for use as an add-on therapy to pridopidine in treating a subject afflicted with ALS.

The invention also provides for a compound which is dextromethorphan/quinidine for use as an add-on therapy to pridopidine in treating a subject afflicted with ALS.

The invention also provides for a compound which is sodium phenylbutyrate (PB) for use as an add-on therapy to pridopidine in treating a subject afflicted with ALS.

The invention also provides for a compound which is tauroursodeoxycholic acid for use as an add-on therapy to pridopidine in treating a subject afflicted with ALS.

The invention also provides for a combination of sodium phenylbutyrate (PB)/tauroursodeoxycholic acid (i.e. AMX0035) for use as an add-on therapy to pridopidine in treating a subject afflicted with ALS.

The invention also provides for pridopidine for use as an add-on therapy to a compound which is riluzole in treating a subject afflicted with ALS.

The invention also provides for pridopidine for use as an add-on therapy to a compound which is edaravone in treating a subject afflicted with ALS.

The invention also provides for pridopidine for use as an add-on therapy to a compound which is dextromethorphan/quinidine in treating a subject afflicted with ALS.

The invention also provides for pridopidine for use as an add-on therapy to a compound which is laquinimod in treating a subject afflicted with ALS.

The invention also provides for pridopidine for use as an add-on therapy to a compound which is sodium phenylbutyrate (PB) in treating a subject afflicted with ALS.

The invention also provides for pridopidine for use as an add-on therapy to a compound which is tauroursodeoxycholic acid in treating a subject afflicted with ALS.

The invention also provides for pridopidine for use as an add-on therapy to a combination of sodium phenylbut rate (PB)/tauroursodeoxycholic acid (i.e. AMX0035) in treating a subject afflicted with ALS.

In an embodiment the add-on therapy is for the treatment, prevention, or alleviation of a symptom of ALS.

The invention also provides for a combination of a compound which is riluzole and pridopidine for use in the treatment, prevention, or alleviation of a symptom of ALS.

The invention also provides for a combination of a compound which is edaravone and pridopidine for use in the treatment, prevention, or alleviation of a symptom of ALS.

The invention also provides for a combination of a compound which is dextromethorphan/quinidine and pridopidine for use in the treatment, prevention, or alleviation of a symptom of ALS.

The invention also provides for a combination of a compound which is sodium phenylbutyrate (PB) and pridopidine for use in the treatment, prevention, or alleviation of a symptom of ALS.

The invention also provides for a combination of a compound which is tauroursodeoxycholic acid and pridopidine for use in the treatment, prevention, or alleviation of a symptom of ALS.

The invention also provides for a combination of combination of sodium phenylbutyrate (PB)/tauroursodeoxycholic acid (i.e. AMX0035) and pridopidine for use in the treatment, prevention, or alleviation of a symptom of ALS The invention also provides for the use of pridopidine in the manufacture of a medicament for the treatment of ALS.

The method, use and composition further include decreasing the rate of neurological deterioration in the subject.

In an embodiment, the methods of the present invention further comprise administering to the subject a therapeutically effective amount of a second compound which is riluzole or edaravone. In an embodiment, the methods of the present invention further comprise administering to the subject a therapeutically effective amount of a second compound which is dextromethorphan/quinidine. In an embodiment, the methods of the present invention further comprise administering to the subject a therapeutically effective amount of a second compound which is sodium phenylbutyrate (PB), or tauroursodeoxycholic acid. In an embodiment, the methods of the present invention further comprise administering to the subject a therapeutically effective amount of a combination of sodium phenylbutyrate (PB)/tauroursodeoxycholic acid (i.e. AMX0035). In an embodiment, the second compound is riluzole. In another embodiment, the second compound is edaravone. In another embodiment, the second compound is dextromethorphan/quinidine. In another embodiment, the second compound is laquinimod. In another embodiment, the second compound is sodium phenylbutyrate (PB), or tauroursodeoxycholic acid.

In an embodiment of the invention, pridopidine and the second compound are administered in one unit. In another embodiment the pridopidine and the second compound are administered in more than one unit.

In an embodiment, the amount of pridopidine and the amount of the second compound are administered simultaneously. In an embodiment, the amount of pridopidine and the amount of the second compound are administered contemporaneously.

In another embodiment, the administration of the second compound precedes the administration of pridopidine. In another embodiment, the administration of pridopidine precedes the administration of the second compound.

In an embodiment, a subject is receiving edaravone therapy prior to initiating pridopidine therapy. In another embodiment, a subject is receiving riluzole prior to initiating pridopidine therapy. In another embodiment, a subject is receiving laquinimod prior to initiating pridopidine therapy. In another embodiment, a subject is receiving dextromethorphan/quinidine prior to initiating pridopidine therapy. In another embodiment, a subject is receiving sodium phenylbutyrate (PB) prior to initiating pridopidine therapy. In another embodiment, a subject is receiving tauroursodeoxycholic acid prior to initiating pridopidine therapy. In another embodiment, a subject is receiving a combination of sodium phenylbutyrate (PB)/tauroursodeoxycholic acid (i.e. AMX0035) prior to initiating pridopidine therapy.

In another embodiment, a subject is receiving edaravone therapy for at least 24 weeks, 28 weeks, 48 weeks, or 52 weeks prior to initiating pridopidine therapy. In another embodiment, a subject is receiving riluzole therapy for at least 24 weeks, 28 weeks, 48 weeks, or 52 weeks prior to initiating pridopidine therapy. In another embodiment, a subject is receiving dextromethorphan/quinidine therapy for at least 1 week, 2 weeks, 4 weeks, or 6 weeks prior to initiating pridopidine therapy. In another embodiment, a subject is receiving sodium phenylbutyrate (PB) therapy for at least 1 week, 2 weeks, 4 weeks, or 6 weeks prior to initiating pridopidine therapy. In another embodiment, a subject is receiving tauroursodeoxycholic acid therapy for at least 1 week, 2 weeks, 4 weeks, or 6 weeks prior to initiating pridopidine therapy. In another embodiment, a subject is receiving combination of sodium phenylbutyrate (PB)/tauroursodeoxycholic acid (i.e. AMX0035) therapy for at least 1 week, 2 weeks, 4 weeks, or 6 weeks prior to initiating pridopidine therapy.

In an embodiment, a subject is receiving pridopidine therapy prior to initiating edaravone therapy. In another embodiment, a subject is receiving pridopidine therapy for at least 24 weeks, 28 weeks, 48 weeks, or 52 weeks prior to initiating edaravone therapy.

In an embodiment, a subject is receiving pridopidine therapy prior to initiating riluzole therapy. In another embodiment, a subject is receiving pridopidine therapy for at least 24 weeks, 28 weeks, 48 weeks, or 52 weeks prior to initiating riluzole therapy.

In an embodiment, a subject is receiving pridopidine therapy prior to initiating laquinimod therapy. In another embodiment, a subject is receiving pridopidine therapy for at least 24 weeks, 28 weeks, 48 weeks, or 52 weeks prior to initiating laquinimod therapy.

In an embodiment, a subject is receiving pridopidine therapy prior to initiating dextromethorphan/quinidine therapy. In another embodiment, a subject is receiving pridopidine therapy for at least 24 weeks, 28 weeks, 48 weeks, or 52 weeks prior to initiating dextromethorphan/quinidine therapy.

In an embodiment, a subject is receiving pridopidine therapy prior to initiating sodium phenylbutyrate (PB), tauroursodeoxycholic acid or combination of sodium phenylbutyrate (PB)/tauroursodeoxycholic acid (i.e. AMX0035) therapy. In another embodiment, a subject is receiving pridopidine therapy for at least 24 weeks, 28 weeks, 48 weeks, or 52 weeks prior to initiating sodium phenylbutyrate (PB), tauroursodeoxycholic acid or combination of sodium phenylbutyrate (PB)/tauroursodeoxycholic acid (i.e. AMX0035) therapy.

In an embodiment, between 0.5 mg to 1.5 mg laquinimod is administered to the patient per day. In another embodiment, 0.5 mg or 1.0 mg laquinimod is administered to the patient per day. In an embodiment, laquinimod is administered orally.

In an embodiment, between 10-200 mg riluzole is administered to the patient per day. In another embodiment, 50 mg, 100 mg, or 200 mg riluzole is administered to the patient per day.

In an embodiment, riluzole is administered orally. In an embodiment dextromethorphan/quinidine is administered orally.

In an embodiment sodium phenylbutyrate (PB) is administered orally. In another embodiment, sodium phenylbutyrate (PB) between 1-10 gr/day is administered to the patient per day. In another embodiment, between 1-5 gr/day, 1-3 gr/day, 4-10 gr/day. In another embodiment, sodium phenylbutyrate (PB) is administered once a day, twice a day or more than twice a day.

In an embodiment tauroursodeoxycholic acid is administered orally. In another embodiment, tauroursodeoxycholic acid between 0.5-3 gr/day is administered to the patient per day. In another embodiment, between 0.5-2 gr/day, 1-3 gr/day. In another embodiment, tauroursodeoxycholic acid is administered once a day, twice a day or more than twice a day.

In an embodiment, AMX0035 is administered orally and is administered to the patient in a therapeutic combination including 3 gr/day of sodium phenylbutyrate and 1 gr/day tauroursodeoxycholic acid (TUDCA) per day, or 9 gr/day of sodium phenylbutmrate and 2 gr/day tauroursodeoxycholic acid (TUDCA) per day. In another embodiment, in a combination including between 1-10 gr/day sodium phenylbutyrate and between 0.5-3 gr/day of tauroursodeoxycholic acid. In another embodiment, AMX0035 is administered once a day, twice a day or more than twice a day.

In an embodiment, between 5-60 mg edaravone is administered to the patient per day. In another embodiment, 30 mg, or 60 mg edaravone is administered to the patient per day.

In an embodiment, edaravone is administered by intravenous infusion. In another embodiment, edaravone is administered once per day for 10 days followed by a 14 day drug-free period. In another embodiment, edaravone is administered once per day for 14 days followed by a 14 day drug-free period.

In an embodiment, each of the amount of the second compound when taken alone, and the amount of pridopidine when taken alone is effective to treat a subject. In another embodiment, either the amount of the second compound when taken alone, the amount of pridopidine when taken alone, is less effective to treat the subject. In another embodiment, either the amount of the second compound when taken alone, the amount of pridopidine when taken alone, is not effective to treat the subject.

In an embodiment, pridopidine is administered adjunctively to the second compound. In another embodiment, the second compound is administered adjunctively to pridopidine.

In an embodiment, a loading dose of an amount different from the intended dose is administered for a period of time at the start of the periodic administration.

In an embodiment provided is a method of enhancing BDNF axonal transport in motor neurons in a subject afflicted with ALS comprising administering to the subject an amount of pridopidine effective to enhance BDNF axonal transport in the subject's motor neurons.

In an embodiment provided is a method of enhancing ERK activation in motor neurons of a subject afflicted with ALS comprising administering to the subject an amount of pridopidine effective to enhance ERK activation in the subject's motor neurons.

In an embodiment provided is a method of preserving neuromuscular junction (NMJ) structure in muscle cells of a subject afflicted with ALS comprising administering to the subject an amount of pridopidine effective to preserving neuromuscular junction structure in the subject's muscles.

Further provided is a method of improving muscle contraction in a subject afflicted with ALS comprising administering to the subject an amount of pridopidine effective to improve muscle contraction function in the subject.

Further provided is a method of improving innervation rate of muscle tissue in a subject afflicted with ALS comprising administering to the subject an amount of pridopidine effective to improve the innervation rate in the subject.

In an embodiment, provided is a method of enhancing motor neuron axonal growth in a subject afflicted with ALS comprising administering to the subject an amount of pridopidine effective to enhance motor neuron axonal growth in the subject.

In an embodiment, provided is a method of enhancing muscle cell survival in a subject afflicted with ALS comprising administering to the subject an amount of pridopidine effective to enhancing muscle cell survival in the subject.

In an embodiment, provided is a method of reducing progression of muscle fiber wasting in a subject afflicted with ALS comprising administering to the subject an amount of pridopidine effective to reduce progression of muscle fiber wasting in the subject.

In an embodiment, provided is a method of reducing axonal degeneration in a subject afflicted with ALS comprising administering to the subject an amount of pridopidine effective to reduce axonal degeneration in the subject.

In an embodiment, provided is a method of preserving NMJ formation in a subject afflicted with ALS comprising administering to the subject an amount of pridopidine effective to preserve NMJ formation in the subject.

In an embodiment, provided is a method of preserving NMJ structure and function in a subject afflicted with ALS comprising administering to the subject an amount of pridopidine effective to preserve NMJ structure and function in the subject.

In an embodiment, provided is a method of reducing protein aggregation in a subject afflicted with ALS comprising administering to the subject an amount of pridopidine effective to reduce protein aggregation in the subject.

In an embodiment, provided is a method of attenuating pseudobulbar disease progression in a subject afflicted with ALS comprising administering to the subject an amount of pridopidine effective to attenuate pseudobulbar disease progression in the subject.

The invention also provides for a package comprising:
a pharmaceutical composition comprising an amount of pridopidine; and
optionally instructions for use of the pharmaceutical composition to treat a subject afflicted with ALS.

The invention also provides for a therapeutic package for dispensing to, or for use in dispensing to, a subject, which comprises:
one or more unit doses, each such unit dose comprising an amount of pridopidine thereof, wherein the amount of said pridopidine in said unit dose is effective, upon administration to said subject, to treat ALS in the subject, and
a finished pharmaceutical container therefor, said container containing said unit dose or unit doses, said container optionally further containing or comprising labeling directing the use of said package in the treatment of a subject afflicted with ALS. Such unit dose contains 10-250 mg pridopidine, or for example 10 mg, 22.5 mg, 45 mg, 67.5 mg, 90 mg, or 112.5 mg pridopidine.

The invention also provides for a package comprising:
a first pharmaceutical composition comprising an amount of pridopidine and a pharmaceutically acceptable carrier;
a second pharmaceutical composition comprising an amount of a second compound which is riluzole, edaravone, combination of dextromethorphan/quinidine, sodium phenylbutyrate (PB), tauroursodeoxycholic acid or a combination of sodium phenylbutyrate (PB)/tauroursodeoxycholic acid (i.e. AMX0035) and a pharmaceutically acceptable carrier; and
optionally instructions for use of the first and second pharmaceutical compositions together to treat a subject afflicted with ALS.

In an embodiment, the amount of the second compound and the amount of pridopidine are prepared to be administered simultaneously or contemporaneously.

The invention also provides for a therapeutic package for dispensing to, or for use in dispensing to, a subject afflicted with ALS, which comprises:
one or more unit doses, each such unit dose comprising:
an amount of pridopidine and
an amount of a second compound which is riluzole, or edaravone, combination of dextromethorphan/quinidine, sodium phenylbutyrate (PB), tauroursodeoxycholic acid or a combination of sodium phenylbutyrate (PB)/tauroursodeoxycholic acid (e AMX0035) wherein the respective amounts of said pridopidine and the second compound in said unit dose are effective, upon concomitant administration to said subject, to treat the subject, and
a finished pharmaceutical container therefor, said container containing said unit dose or unit doses, said container optionally further containing or comprising labeling directing the use of said package in the treatment of said subject.

The invention further provides a method for combination therapy for treatment of ALS comprising administering to a subject in need thereof a therapeutically effective amount of pridopidine and therapeutically effective amount of riluzole, edaravone, combination of dextromethorphan/quinidine, sodium phenylbutyrate (PB), tauroursodeoxycholic acid or a combination of sodium phenylbutyrate (PB)/tauroursodeoxycholic acid (i.e. AMX0035).

For the foregoing embodiments, each embodiment disclosed herein is contemplated as being applicable to each of the other disclosed embodiments. For instance, the elements recited in the method embodiments can be used in the pharmaceutical composition, package, and use embodiments described herein and vice versa.

All combinations, sub-combinations, and permutations of the various elements of the methods and uses described herein are envisaged and are within the scope of the invention.

Pharmaceutically Acceptable Salts

As used herein, "pridopidine" means pridopidine base or a pharmaceutically acceptable salt thereof, as well as derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. In certain embodiments, pridopidine is a pharmaceutically acceptable salt, such as the HCl salt or tartrate salt. Preferably, in any embodiments of the invention as described herein, the pridopidine is in the form of its hydrochloride salt.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methane sulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

"Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials Pharmaceutical Compositions While the pridopidine for use according to the invention may be administered in the form of the raw compound, preferred administration of pridopidine, optionally in the form of a physiologically acceptable salt, is in a pharmaceutical composition together with one or more adjuvants, excipients, carriers, buffers, diluents, and/or other customary pharmaceutical auxiliaries.

In an embodiment, the invention provides pharmaceutical compositions comprising the pridopidine or pharmaceutically acceptable salts or derivatives thereof, together with one or more pharmaceutically acceptable carriers therefore, and, optionally, other therapeutic and/or prophylactic ingredients known and used in the art including, but not limited to, riluzole, edaravone Nuedexta® (dextromethorphan/quinidine), sodium phenylbutyrate (PB), tauroursodeoxycholic acid or a combination of sodium phenylbutyrate (PB)/tauroursodcoxycholic acid (i.e. AMX0035).

The carrier(s) must be "acceptable" in the sense of being compatible with the other ingredients of the formulation and suitable for administration to a human subject.

Combination Therapy

When the invention comprises a combination of the active compound and an additional one, or more, therapeutic and/or prophylactic ingredients, the combination of the invention may be formulated for its simultaneous or contemporaneous administration, with at least a pharmaceutically acceptable carrier, additive, adjuvant or vehicle. This has the implication that the combination of the two active compounds may be administered:

- as a combination that is part of the same medicament formulation, the two active compounds being then administered simultaneously, or
- as a combination of two units, each with one of the active substances giving rise to the possibility of simultaneous or contemporaneous administration.

The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999).

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry, 1999).

In one example, combined administration of GA and interferon (IFN) has been experimentally shown to abrogate the clinical effectiveness of either therapy (Brod 2000). In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Administration

The pharmaceutical composition of the invention may be administered by any convenient route, which suits the desired therapy. Preferred routes of administration include oral administration, in particular in tablet, in capsule, in dragée, in powder, or in liquid form, intranasal administration, intradermal administration, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Tablets may contain suitable binders, lubricants, disintegrating agents (disintegrants), coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators (disintegrants) include, without limitation, starch, methyl cellulose, agar, bentonite, xanthan gum, croscarmellose sodium, sodium starch glycolate and the like.

General techniques and compositions for making dosage forms useful in the present invention are described in the following references: Modern Pharmaceutics, Chapters 9 and 10 (Banker & Rhodes, Editors, 1979); Pharmaceutical Dosage Forms: Tablets (Lieberman 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995): Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds); Modern Pharmaceutics Drugs and the Pharmaceutical Sciences, Vol. 40 (Gilbert S. Banker, Christopher T. Rhodes, Eds). These references in their entireties are hereby incorporated by reference into this application.

Terms

As used herein, and unless stated otherwise, each of the following terms shall have the definition set forth below.

As used herein, "riluzole" means riluzole or a pharmaceutically acceptable salt thereof, as well as derivatives, for example deuterium-enriched version of riluzole and salts. Riluzole is descried in Prescribers' Digital Reference which is hereby incorporated by reference (Riluzole PDR 2017).

As used herein, "edaravone" means edaravone or a pharmaceutically acceptable salt thereof, as well as derivatives, for example deuterium-enriched version of edaravone and salts. Edaravone is descried in Prescribers' Digital Reference which is hereby incorporated by reference (Edaravone PDR 2017).

As used herein. "AMX0035" means an oral combination of two drugs already in use, sodium phenylbutyrate (PB) and tauroursodeoxycholic acid (TUDCA). AMX0035 is a combination therapy designed to reduce neuronal death through blockade of key cellular death pathways originating in the mitochondria and endoplasmic reticulum (ER).

A "combination of dextromethorphan and quinidine" or "dextromethorphan/quinidine" or "dextromethorphan hydrobromide/quinidine sulfate" refers to a combination of dextromethorphan hydrobromide (20 mg) and quinidine sulfate (10 mg) such as Nuedexta®. Nuedexta® is a drug currently on the market for treating pseudobulbar affect (PBA) in, inter alia, ALS patients. Nuedexta® has been shown to act on sigma-1 and NMDA receptors in the brain. Recent data demonstrate that the combination has an effect on bulbar function in ALS, but not on other aspects of motor functions (Smith 2017). Dextromethorphan hydrobromide/quinidine sulfate is descried in Prescribers' Digital Reference which is hereby incorporated by reference (Dextromethorphan hydrobromide/quinidine sulfate PDR 2017).

As used herein, an "amount" or "dose" of pridopidine as measured in milligrams refers to the milligrams of underivatized pridopidine base present in a preparation, regardless of the form of the preparation. A "dose of 45 mg pridopidine" means the amount of pridopidine in a preparation is sufficient to provide 45 mg of underivatized pridopidine base having a naturally occurring isotope distribution, regardless of the form of the preparation. Thus, when in the form of a salt, e.g. a pridopidine hydrochloride, the mass of the salt form necessary to provide a dose of 45 mg underivatized pridopidine base would be greater than 45 mg due to the presence of the additional salt ion. Similarly, when in the form of a deuterium-enriched derivative, the mass of the derivatized form necessary to provide a dose of 45 mg underivatized pridopidine base having a naturally occurring isotope distribution would be greater than 45 mg due to the presence of the additional deuterium.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1; 0.2 . . . 0.9; and 1, 2 . . . 49 mg unit amounts are included as embodiments of this invention. By any range of time disclosed herein (i.e. weeks, months, or years), it is meant that all lengths of time of days and/or weeks within the range are specifically disclosed as part of the invention. Thus, for example, 3-6 months means that 3 months and 1 day, 3 months and 1 week, and 4 months are included as embodiments of the invention.

As used herein, "about" in the context of a numerical value or range means±10% of the numerical value or range recited or claimed.

As used herein, "monotherapy" means treatment with a single active agent, for example treatment with pridopidine alone.

As used herein, "adjunctively" means treatment with or administration of an additional compound, with a primary compound, for example for increasing the efficacy or safety of the primary compound or for facilitating its activity.

As used herein. "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times a week and so on, etc.

As used herein, "combination" means an assemblage of reagents for use in therapy either by simultaneous or contemporaneous administration. Simultaneous administration refers to administration of an admixture (whether a true mixture, a suspension, an emulsion or other physical combination) of the pridopidine and a second compound (for example, riluzole). In this case, the combination may be the admixture or separate containers of the pridopidine and the second compound that are combined just prior to administration. Contemporaneous administration, or concomitant administration refer to the separate administration of the pridopidine and the second compound (for example, riluzole) at the same time, or at times sufficiently close together that an additive or preferably synergistic activity relative to the activity of either the pridopidine or the second compound alone is observed or in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine therapy to a patient already receiving riluzole therapy.

As used herein, "effective" when referring to an amount of pridopidine refers to the quantity of pridopidine that is sufficient to yield a desired therapeutic response. In a preferred embodiment, the quantity of pridopidine administered does not result in adverse side-effects (such as toxicity, irritation, or allergic response).

"Administering to the subject" or "administering to the (human) patient" means the giving of, dispensing of, or application of medicines, drugs, or remedies to a subject/patient to relieve, cure, or reduce the symptoms associated with a disease, disorder or condition, e.g., a pathological condition.

"Treating" as used herein encompasses inducing inhibition, regression, or stasis of a disease or disorder, or lessening, suppressing, inhibiting, reducing the severity of, eliminating or substantially eliminating, or ameliorating a symptom of the disease or disorder.

"Inhibition" of disease progression or disease complication in a subject means preventing or reducing the disease progression and/or disease complication in the subject.

A "symptom" associated with a disease or disorder includes any clinical or laboratory manifestation associated with the disease or disorder and is not limited to what the subject can feel or observe.

As used herein, "a subject afflicted with" a disease, disorder or condition means a subject who has been clinically diagnosed to have the disease, disorder or condition.

Glial cell-derived neurotrophic factor (GDNF) is a protein encoded by the GDNF gene and is believed to promote the survival of many types of neurons them.

Brain-derived neurotrophic factor (BDNF), is a protein produced by neurons and serves to keep functioning and to promote the growth of neurons and neurogenesis.

The following numbered clauses define various aspects and features of the present invention:

1. A method for treating a subject afflicted with amyotrophic lateral sclerosis (ALS), comprising periodically administering to the subject an amount of pridopidine effective to treat the subject.
2. The method of clause 1, wherein the amount of pridopidine is effective to inhibit or reduce progression of a symptom of the ALS in the subject.
3. The method of clause 2, where in the symptom is muscles stiffness, muscle weakness, muscle wasting, muscle cramps, difficulty speaking, difficulty swallowing, difficulty breathing, difficulty chewing, difficulty walking, fasciculations, and/or worsening posture.
4. The method of any one of clauses 1-3, wherein the ALS is sporadic ALS.
5. The method of any one of clauses 1-4, wherein the amount of pridopidine is administered daily or wherein the amount of pridopidine is administered more often than once daily.
6. The method of any one of clauses 1-4, wherein the amount of pridopidine is administered twice daily.
7. The method of any one of clauses 1-4, wherein the amount of pridopidine is administered less often than once daily.
8. The method of any one of clauses 1-7, wherein the amount of pridopidine is administered orally.
9. The method of any one of clauses 1-8, wherein the amount of pridopidine administered is from 22.5 mg per day to 225 mg per day.
10. The method of clause 9, wherein the amount of pridopidine administered is from 45 mg per day to 180 mg per day.
11. The method of clause 9, wherein the amount of pridopidine administered is 5 mg, 10 mg, 22.5 mg, 45 mg, 67.5, mg, 90 mg, 100 mg, 112.5 mg, 125 mg, 135 mg, 150 mg, or 180 mg per day.
12. The method of any one of clauses 1-11, wherein the periodic administration continues for at least 24 weeks.
13. The method of any one of clauses 1-12, wherein the pridopidine is pridopidine hydrochloride.
14. The method of any one of clauses 1-13, wherein the subject is a human subject.
15. The method of any one of clauses 1-14, further comprising administering to the subject a therapeutically effective amount of a second compound.
16. The method of clause 15, wherein the second compound is riluzole, edaravone or dextromethorphan/quinidine, sodium phenylbutyrate (PB), tauroursodeoxycholic acid or sodium phenylbutyrate (PB)/tauroursodeoxycholic acid (i.e. AMX0035).
17. The method of clauses 15-16, wherein the pridopidine and the second compound are administered in one unit.
18. The method of clauses 15-16, wherein the pridopidine and the second compound are administered in more than one unit.
19. The method of any one of clauses 15-18, wherein the second compound is riluzole.
20. The method of clause 19, wherein 10 mg-200 mg or 50 mg, 100 mg or 200 mg of riluzole is administered to the subject per day.
21. The method of any one of clauses 15-20, wherein the riluzole is administered orally.
22. The method of any one of clauses 15-18, wherein the second compound is edaravone.
23. The method of clause 22, wherein 5-60 mg or 30 mg or 60 mg of edaravone is administered to the subject per day.
24. The method of any one of clauses 15-18 and 22-23, wherein the edaravone is administered by intravenous infusion.
25. The method of any one of clauses 15-18 and 22-24, where the edaravone is administered once per day for 14 days or 10 days followed by a 14 day drug-free period.
26. The method of any one of clauses 15-18, wherein the second compound is dextromethorphan/quinidine.
27. The method of clause 26, wherein 10, 20, or 40 mg of dextromethorphan is administered to the subject per day and 5, 10 or 20 mg of quinidine is administered to the subject per day.
28. The method of any one of clauses 26-27, wherein the dextromethorphan/quinidine is administered orally.
29. The method of any one of clauses 15-28, wherein the amount of pridopidine and the amount of the second compound are administered simultaneously.
30. The method of any one of clauses 15-28, wherein the administration of the second compound substantially precedes the administration of pridopidine.
31. The method of any one of clauses 15-28, wherein the administration of pridopidine substantially precedes the administration of the second compound.
32. The method of any one of clauses 15-28, wherein the subject is receiving edaravone therapy, dextromethorphan/quinidine therapy, or riluzole therapy prior to initiating pridopidine therapy.
33. The method of clause 32, wherein the subject is receiving edaravone therapy, dextromethorphan/quinidine therapy or riluzole therapy for at least 24 weeks, 28 weeks, 48 weeks, or 52 weeks prior to initiating pridopidine therapy.
34. The method of any one of clauses 15-28, wherein the subject is receiving pridopidine therapy prior to initiating edaravone therapy, dextromethorphan/quinidine therapy or riluzole therapy.
35. The method of clause 34, wherein the subject is receiving pridopidine therapy for at least 24 weeks, 28 weeks, 48 weeks, or 52 weeks prior to initiating edaravone therapy, dextromethorphan/quinidine therapy, or riluzole therapy.
36. The method of any one of clauses 15-35, wherein each of the amount of the second compound when taken alone, and the amount of pridopidine when taken alone is effective to treat the subject.
37. The method of any one of clauses 15-35 wherein either the amount of the second compound when taken alone, the amount of pridopidine when taken alone, or each such amount when taken alone is not effective to treat the subject.
38. The method of any one of clauses 15-35, wherein either the amount of the second compound when taken alone, the amount of pridopidine when taken alone, or each such amount when taken alone is less effective to treat the subject.
39. The method of any one of clauses 15-38, wherein the pridopidine is administered adjunctively to the second compound.
40. The method of any one of clauses 15-38, wherein the second compound is administered adjunctively to the pridopidine.
41. The method of any one of clauses 1-40, wherein a loading dose of an amount different from the intended dose is administered for a period of time at the start of the periodic administration.
42. A method of enhancing BDNF axonal transport in motor neurons in a subject afflicted with ALS comprising administering to the subject an amount of pridopidine effective to enhance BDNF axonal transport in the subject's motor neurons.

43. A method of improving NMJ formation and function in a subject afflicted with ALS comprising administering to the subject an amount of pridopidine effective to improve NMJ formation and muscle contraction function in the subject.

44. A method of improving innervation rate of muscle tissue in a subject afflicted with ALS comprising administering to the subject an amount of pridopidine effective to improve innervation rate in the subject.

45. A method of enhancing motor neuron axonal growth in a subject afflicted with ALS comprising administering to the subject an amount of pridopidine effective to enhance motor neuron axonal growth in the subject.

46. A method of enhancing muscle contraction in a subject afflicted with ALS comprising administering to the subject an amount of pridopidine effective to enhance the muscle contraction in the subject.

47. A method of restoring muscle contraction in a subject afflicted with ALS comprising administering to the subject an amount of pridopidine effective to improve the muscle contraction in the subject.

48. A pharmaceutical composition comprising an effective amount of pridopidine for use in treating a subject afflicted with ALS.

49. Use of an amount of pridopidine for the manufacture of a medicament for use in treating a subject afflicted with ALS.

50. A package comprising:
a) a pharmaceutical composition comprising an amount of pridopidine; and optionally
b) instructions for use of the pharmaceutical composition to treat a subject afflicted with ALS.

51. A therapeutic package for dispensing to, or for use in dispensing to, a subject, which comprises:
a) one or more unit doses, each such unit dose comprising an amount of pridopidine thereof, wherein the amount of said pridopidine in said unit dose is effective, upon administration to said subject, to treat ALS in the subject, and
b) a finished pharmaceutical container therefor, said container containing said unit dose or unit doses, said container further containing or comprising labeling directing the use of said package in the treatment of a subject afflicted with ALS.

52. A package comprising:
a) a first pharmaceutical composition comprising an amount of pridopidine and a pharmaceutically acceptable carrier;
b) a second pharmaceutical composition comprising an amount of a second compound which is riluzole, edaravone, dextromethorphan/quinidine, sodium phenylbutyrate (PB), tauroursodeoxycholic acid or sodium phenylbutyrate (PB)/ tauroursodeoxycholic acid (i.e. AMX0035) and a pharmaceutically acceptable carrier; and optionally
c) instructions for use of the first and second pharmaceutical compositions together to treat a subject afflicted with ALS.

53. The package of clause 52, wherein the amount of the second compound and the amount of pridopidine are prepared to be administered simultaneously or contemporaneously.

54. A therapeutic package for dispensing to, or for use in dispensing to, a subject afflicted with ALS, which comprises:
a) one or more unit doses, each such unit dose comprising:
i) an amount of pridopidine and
ii) an amount of a second compound which is riluzole, edaravone or dextromethorphan/quinidine;

wherein the respective amounts of said pridopidine and the second compound in said unit dose are effective, upon concomitant administration to said subject, to treat the subject, and
b) a finished pharmaceutical container therefor, said container containing said unit dose or unit doses, said container further containing or comprising labeling directing the use of said package in the treatment of said subject.

55. A pharmaceutical composition comprising an amount of pridopidine and an amount of a second compound which is riluzole, edaravone or dextromethorphan/quinidine.

56. The pharmaceutical composition of clause 55 for use in treating a subject afflicted with ALS, wherein the pridopidine and the second compound are prepared to be administered simultaneously, contemporaneously or concomitantly.

57. A pharmaceutical composition in unit dosage form, useful in treating a subject afflicted with ALS, which comprises:
a) an amount of pridopidine;
b) an amount of second compound which is riluzole, edaravone or dextromethorphan/quinidine,
wherein the respective amounts of said second compound and said pridopidine in said composition are effective, upon concomitant administration to said subject of one or more of said unit dosage forms of said composition, to treat the subject.

58. A pharmaceutical composition comprising an amount of pridopidine for use in treating a subject afflicted with ALS as an add-on therapy to a second compound which is riluzole, edaravone or dextromethorphan/quinidine.

59. A pharmaceutical composition comprising an amount of pridopidine for use in treating a subject afflicted with ALS simultaneously, contemporaneously or concomitantly with a second compound which is riluzole, edaravone or dextromethorphan/quinidine.

60. A pharmaceutical composition comprising an amount of a compound which is riluzole, edaravone or dextromethorphan/quinidine for use in treating a subject afflicted with ALS as an add-on therapy to pridopidine.

61. A pharmaceutical composition comprising an amount of a compound which is riluzole, edaravone or dextromethorphan/quinidine for use in treating a subject afflicted with ALS simultaneously, contemporaneously or concomitantly with pridopidine.

62. A compound which is riluzole, edaravone or dextromethorphan/quinidine for use as an add-on therapy to pridopidine in treating a subject afflicted with ALS.

63. Pridopidine for use as an add-on therapy to a compound which is riluzole, edaravone or dextromethorphan/quinidine in treating a subject afflicted with ALS.

64. The add-on therapy of clause 63, wherein the therapy is for the treatment, prevention, or alleviation of a symptom of ALS.

65. A combination of pridopidine with a compound which is riluzole, edaravone or dextromethorphan/quinidine for use in the treatment, prevention, or alleviation of a symptom of ALS.

Throughout this application, certain publications and patent application publications are referenced. Full citations for the publications may be found immediately preceding the claims. The disclosures of these publications and patent application publications in their entireties are hereby incorporated by reference into this application in order to describe more fully the state of the art to which this invention relates.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Experiment 1: Axonal Transport Assays

Healthy motor neurons (MN) extend axons over long distances and through varying extracellular microenvironments to form synapses with muscles. The ability of the neuron to maintain this specialized morphology depends on cytoskeletal elements and continuous transport of proteins and organelles to and from the cell body. Cytoskeletal alterations are a major pathway implicated in the pathogenesis of ALS affecting axonal transport, growth and neuromuscular junction (NMJ) function (Eykens and Robberecht, 2015). Alterations in axonal transport are one of the first cellular processes that occur in neurodegenerative disease, including ALS. Axonal transport was evaluated using an in vitro compartmentalized system of microfluidic chambers (MFC) that separates neuronal cell bodies from their axons and synapses, enabling the study of retrograde/anterograde transport by specific monitoring and manipulation of cellular microenvironments (FIG. 1b: Zahavi 2015; Ionescu 2016).

Quantum-Dot labeled BDNF (Qdot BDNF) is retrogradely transported in axons of motor neurons grown from spinal cord explants in a microfluidic chamber (MFC). A MFC was used to analyze Qdot BDNF axonal transport. Axonal transport of BDNF in the SOD1 model (SOD1G93A) for ALS has been studied (Bilsland 2010; Perlson 2009; De Vos 2007). The effect of pridopidine on transport of Qdot BDNF along the axons of motor neurons was assessed in spinal cord explants from E12.5 SOD1 G93A and WT littermate mice (LM). Experimental workflow for the axonal transport assay (from left to right, FIG. 1a): SOD1G93A or wild Type (LM) spinal cord explants were plated in the MFC. At about 5 days post plating, axons began to cross over into the distal compartment. On day 6 post plating, an amount of pridopidine was added to both compartments. On day 7, Qdot-BDNF was added to the distal compartment and axonal transport was imaged using a high-resolution spinning-disk confocal microscope. Schematic illustration of microfluidic chamber system (FIG. 1b): Explants planted in the proximal compartment extend axons to the distal compartment, where Qdot-BDNF is applied exclusively prior to visualization.

Spinning disk confocal microscopy was used to track Qdot BDNF along the axons of motor neuron explant cultures. Time lapse images of Qdot-BDNF axonal transport as acquired at 60× magnification (FIG. 1c). Arrowheads point to a single Qdot-BDNF particle that is retrogradely transported (left) towards the cell body. Scale bar: 10 µm. Bottom panel shows a kymograph of a complete Qdot-BDNF time-lapse movie. Scale bars: horizontal 10 µm: vertical 100 seconds (FIG. 1c).

Figure 1B:
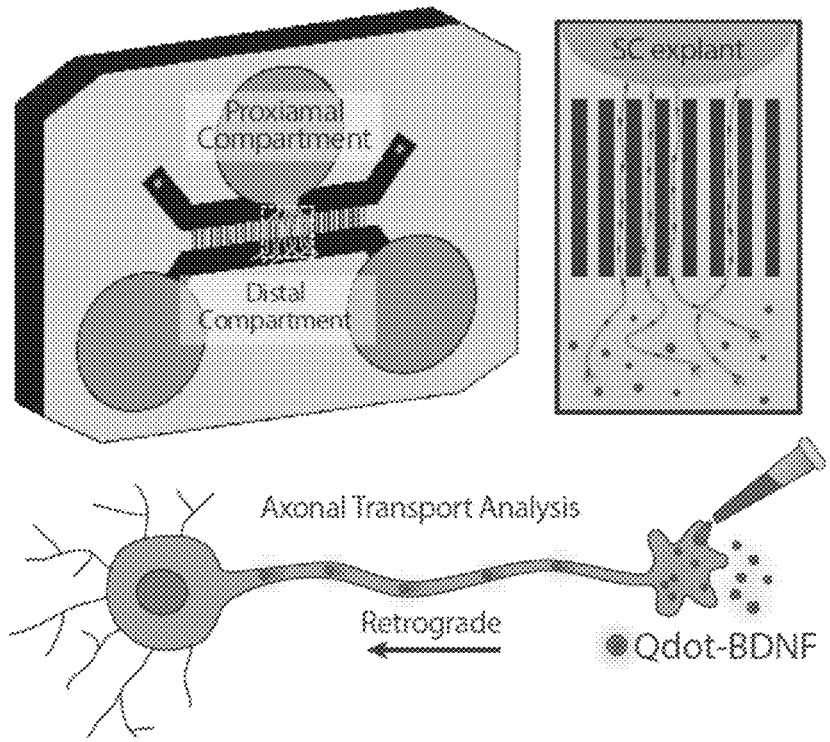
Figure 1C:
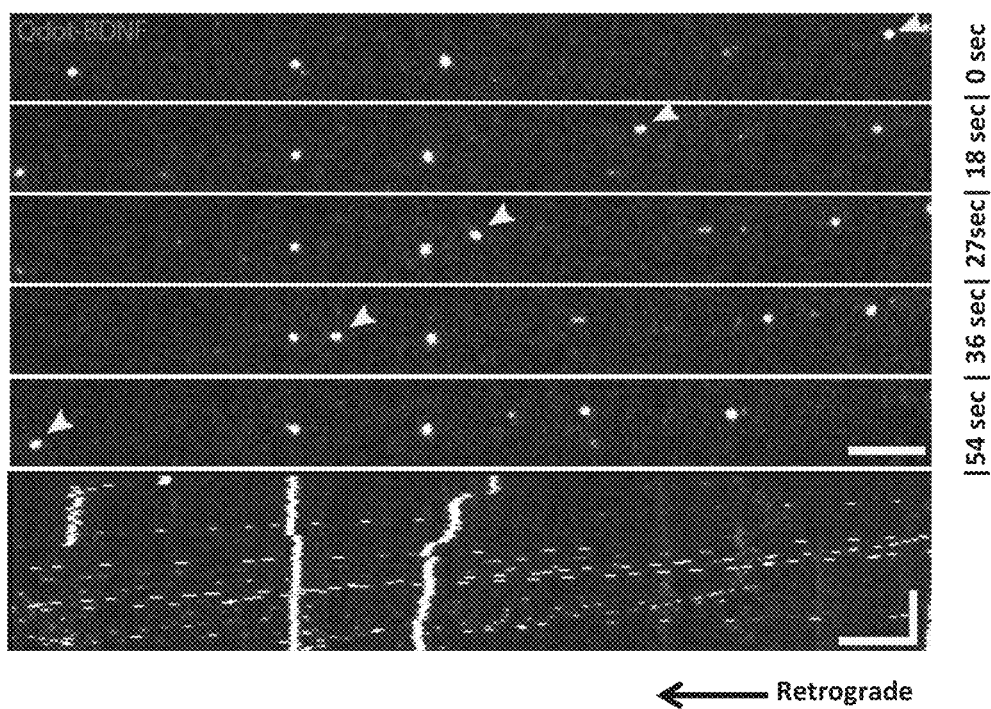

Vehicle and pridopidine were added to both compartments at 2 concentrations (0.1 µM, and 1 µM) on experimental day 6, and Qdot BDNF was added to the distal compartment after overnight incubation with pridopidine (FIGS. 1a and 1b). Six independent biological repeats, from 6 different cultures were tested so that from each culture and explant with neurons/glia ~250 BDNF particles were followed along the axons in the grooves. Velocity refers to the movement of a single BDNF particle. The experiment was repeated with MNs from mice in which sigma 1 receptor was genetically deleted (S1R KO or S1R−/−) (Langa, 2003). Ventral spinal cord sections from S1R−/− mice embryos were cultured and plated in the MFC as described above, and the axonal transport of Qdot-BDNF was analyzed.

SOD1G93 and S1R−/− explants with or without pridopidine were compared to littermate controls (LM).

Qdot-BDNF particle tracking was performed on Bitplane Imaris, using the semi-automated spot tracking function. Inclusion criteria for particle analysis: track duration>10 frames: average velocity≥0.2 µm/sec; stop duration: speed<0.1 µm/sec for 3 frames. Data were then exported to MATLAB for further analysis of particle transport including Instantaneous Velocities (FIG. 2a) from 6 independent cultures, and Stop count (FIG. 2b).

Figure 2A:
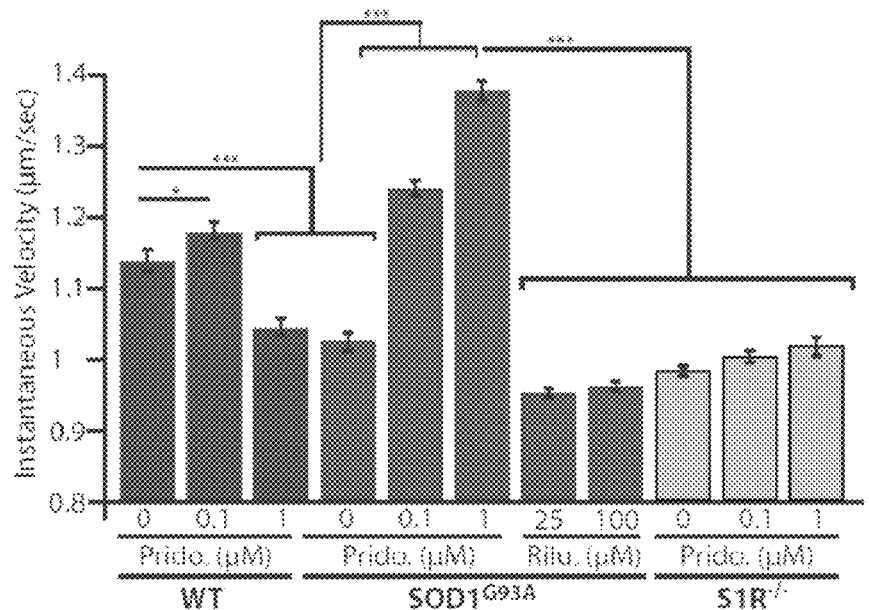
FIGS. 2a-2b. Graphs showing effect of pridopidine on instantaneous velocity values and particle stop count of Qdot-BDNF along the axon (LM (littermate)=WT (wild type)) FIG. 2a. Pridopidine's effect on instantaneous velocity values (µm/sec) for Qdot-BDNF particles in WT (blue), SOD1G93A (red) or Sigma-1 receptor knock out (S1R−/−) (grey) MNs.
Figure 2B:
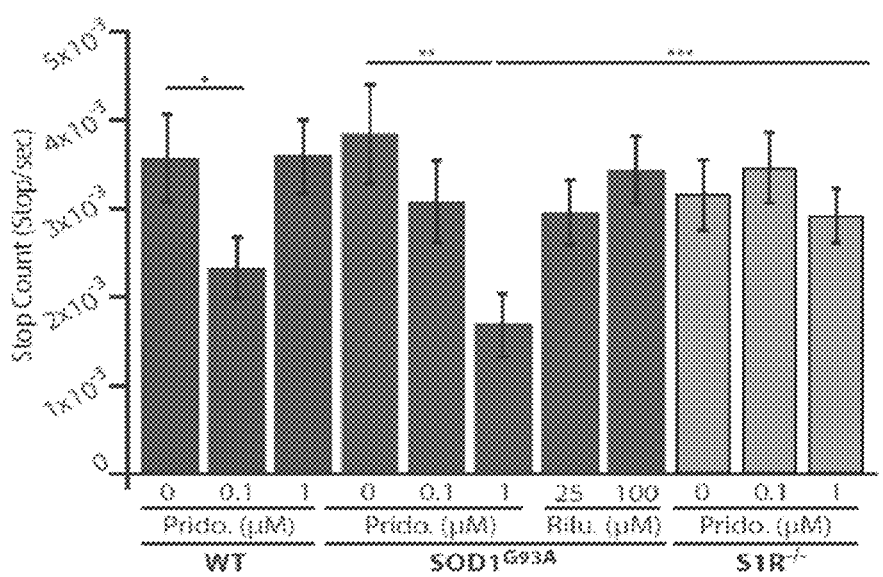

Results:

FIG. 2a demonstrates that pridopidine enhanced BDNF axonal transport instantaneous velocity in SOD1G93A motor neurons. Instantaneous velocity of BDNF retrograde transport is typically reduced in SOD1G93A motor neurons. SOD1G93A MNs show slower velocities vs the WT MNs. Pridopidine treatment accelerated the instantaneous velocities both in WT MNs (0.1 µM) and SOD1G93A MNs (0.1 µM and 1 µM). Application of 25lM or 100l M Riluzole to SOD1G93A MNs did not affect the instantaneous velocities. S1R−/− MNs revealed reduced velocity of BDNF axonal transport. Pridopidine at either 0.1 µM or 1 µM was not able to recover these defects in S1R KO MNs (FIG. 2a).

Particle stop count (number of counted stops of Qdot-BDNF per second), shows that pridopidine reduced the number of pauses during axonal transport in WT MNs (0.1 µM only) and SOD1G93A MNs (both 0.1 µM and 1 µM). Axonal transport parameters of Qdot-BDNF in SiR−/− MNs show that they are not responsive to pridopidine at any of the concentrations tested (FIG. 2b).

These results demonstrate that pridopidine enhanced BDNF axonal transport in SOD1G93A motor neurons and has the capacity to correct ALS related deficits.

Experiment 2: Axon-Muscle Growth/Degeneration Assays

Figure 3:
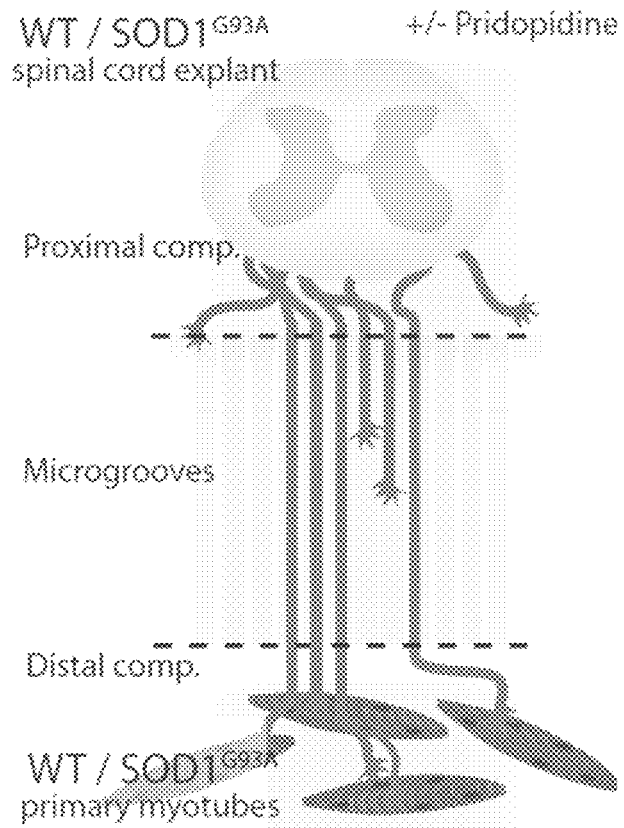
FIG. 3. Schematic illustration of the experimental procedure for neuromuscular coculture assays measuring muscle innervation and Neuro Muscular Junction function (NMJ). Spinal explant is cultured in the proximal compartment and primary myocytes are cultured in the distal compartment.

An early event in the pathogenesis of ALS is axonal degeneration. The compartmental co-culture microfluidic chamber system was used to determine whether pridopidine alters axonal degeneration (FIG. 3). Primary muscle cells from presymptomatic (P60) WT or SOD1G93A mice were cultured. On day 6 primary skeletal myoblasts were cultured in the distal compartment of a MFC. About six days later (day 12), ventral spinal cord explants from WT or SOD1G93A E12.5 mouse embryos that express HB9-GFP (a specific motor neuron marker) were plated in the proximal compartment, followed by application of pridopidine or vehicle to both compartments. Pridopidine was refreshed every other day. Two days post explant plating (day 14), motor axon growth and degeneration were evaluated using live imaging on a spinning disc confocal system. Axonal growth was tracked by imaging every 10 min for 8 hrs. Experiments were repeated three times.

Figure 4:
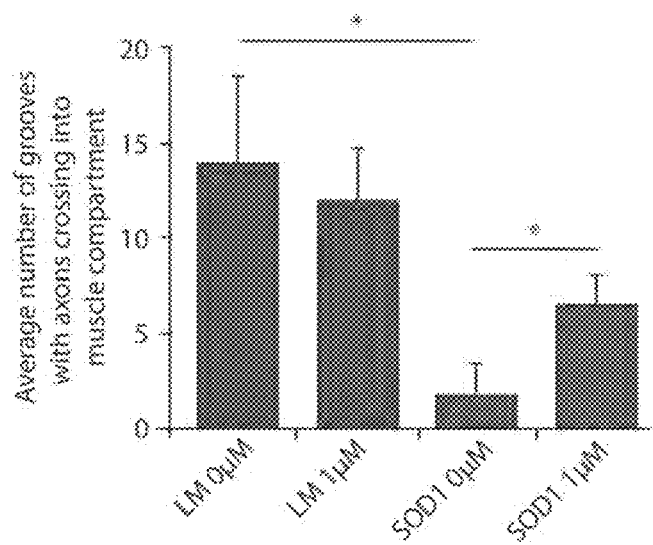
FIG. 4. Graph showing pridopidine's effect on axonal growth for WT and SOD1G93A, which measures the number of grooves with axons crossing into the muscle compartment.

Results:

The data demonstrate that pridopidine increased axonal growth (FIG. 4). Myocytes carrying the SOD1G93A mutation have a reduced number of healthy axons that are able to cross into the distal compartment of the microfluidic compartmental chamber as compared with WT (LM) myocytes. Treatment with 1 µM pridopidine (furthest right bar) showed an increased number of axons crossing into the distal compartment (compartment with muscle cells). (Y axis is average number of grooves with axons crossing into muscle compartment).

These results demonstrate that pridopidine enhanced axonal growth and has the capacity to correct ALS related deficits.

Experiment 3: Measurement of Neuromuscular Junction (NMJ) Formation and Function Synapse disruption is the earliest cellular compartment disrupted in ALS. To test the ability of pridopidine to affect synapse function in an ALS model, cultures from Experiment 2 were grown for approximately four additional days (day 18), when axons extend into the distal compartment and generate NMJs. In this co-culture, MN axons formed NMJs on fully differentiated primary myocytes.

Figure 5A:
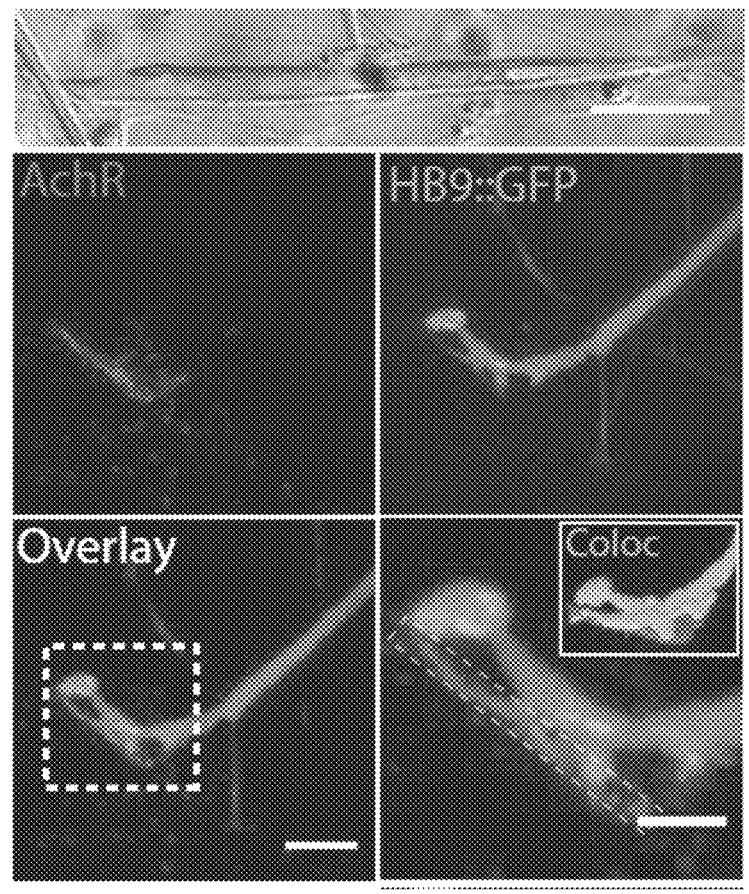
FIGS. 5a and 5b. Results of Micro Fluidic Compartment (MFC) co-culture assays FIG. 5a. Upper panel: Phase image of a myocyte in the distal compartment connected by axons (green arrowheads). Lower panel: High magnification images of myocyte:MN contact points.
Figure 5B:
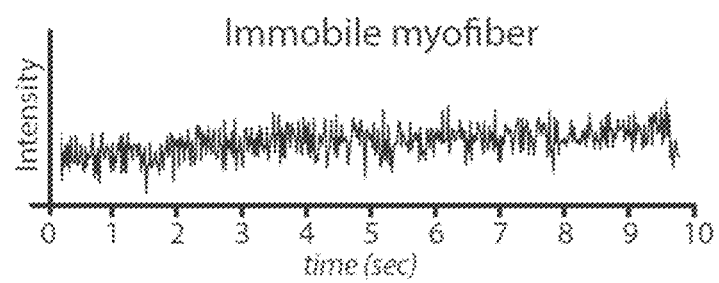
Figure 5B:
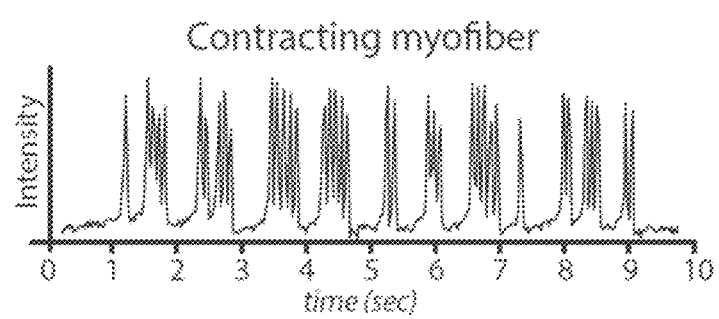

These can be observed by the co-localization of the post-synaptic marker (AchR, ecetyl choline receptor) with the Hb9:GFP neuronal marker. FIG. 5a: Upper panel: Phase-contrast microscope image of a myocyte in the distal compartment connected by axons (arrowheads). Scale bar: 201 µm. Lower panel: High magnification images of myocyte: MN contact points reveal the formation of NMJs as seen by co-localization of post synaptic AChR with HB9::GFP axons and 3-dimensional co-localization of pre and post-synaptic markers (coloc). To evaluate NMJ function, movies of muscle contraction were acquired at a frame rate of 30 frames per second for 1000 frames (FIG. 5b). Muscle contraction traces as extracted from intensity over time measurements of muscle contraction show the flat trace of a non-contracting, immobile myocyte (upper), and the trace of a contracting myocyte demonstrating multiple bursting events (lower).

To study the effect of pridopidine on MN and NMJ formation and function, either 0.1 or 1 µM pridopidine or vehicle were added. Measurement of % innervation and innervation-induced contraction in myotubes was evaluated using live cell imaging as reported before (Ionescu 2015: Zahavi 2015). Briefly, contractile activity of muscles in the distal compartment of the MFC, which were overlapped by at least one axon was examined. Muscles were categorized into two groups: 'Contracting' or 'Non-contracting', depending on their motile activity during the movie. The motility of muscles was validated by generating intensity-over-time plots for each muscle (FIG. 5b). The number of contracting muscle fibers per chamber was divided by the total number of muscle fibers analyzed in the same chamber, yielding the percentage of contracting myotubes as an output for NMJ activity.

Figure 6:
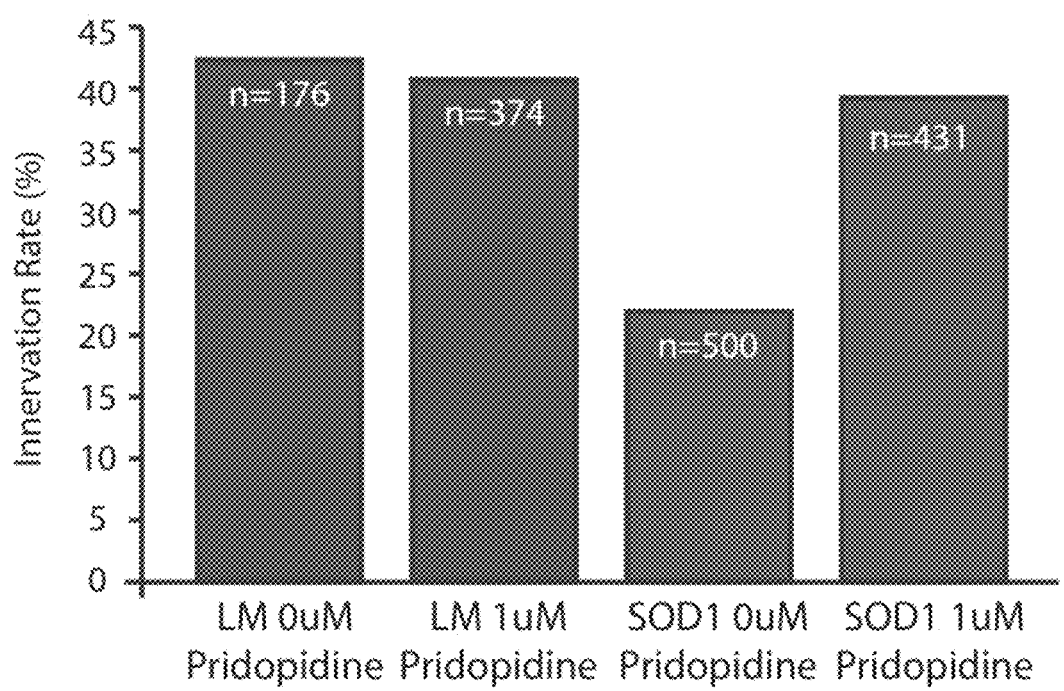
FIG. 6. Graph showing pridopidine's effect on innervation rate in WT and SOD1G93A myocytes.

Results:

Treatment of muscle cells with Pridopidine was able to induce innervation leading to higher likelihood of bursting muscle patterns. Innervation rate of muscles carrying SOD1 mutation is lower compared to WT (wild type) muscles (20% innervation compared to 40% in WTs). Pridopidine at 1 µM increases innervation rate of muscles carrying SOD1 mutation to near WT levels (FIG. 6).

Figure 7A:
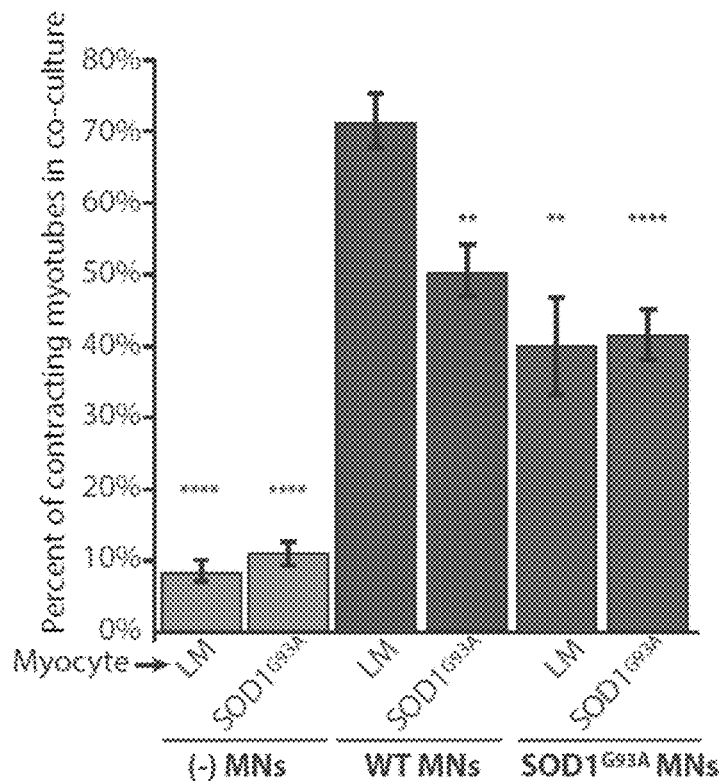
FIGS. 7a-7b. Graphs showing level of contracting myocytes in MN-myocyte co-culture.
Figure 7B:
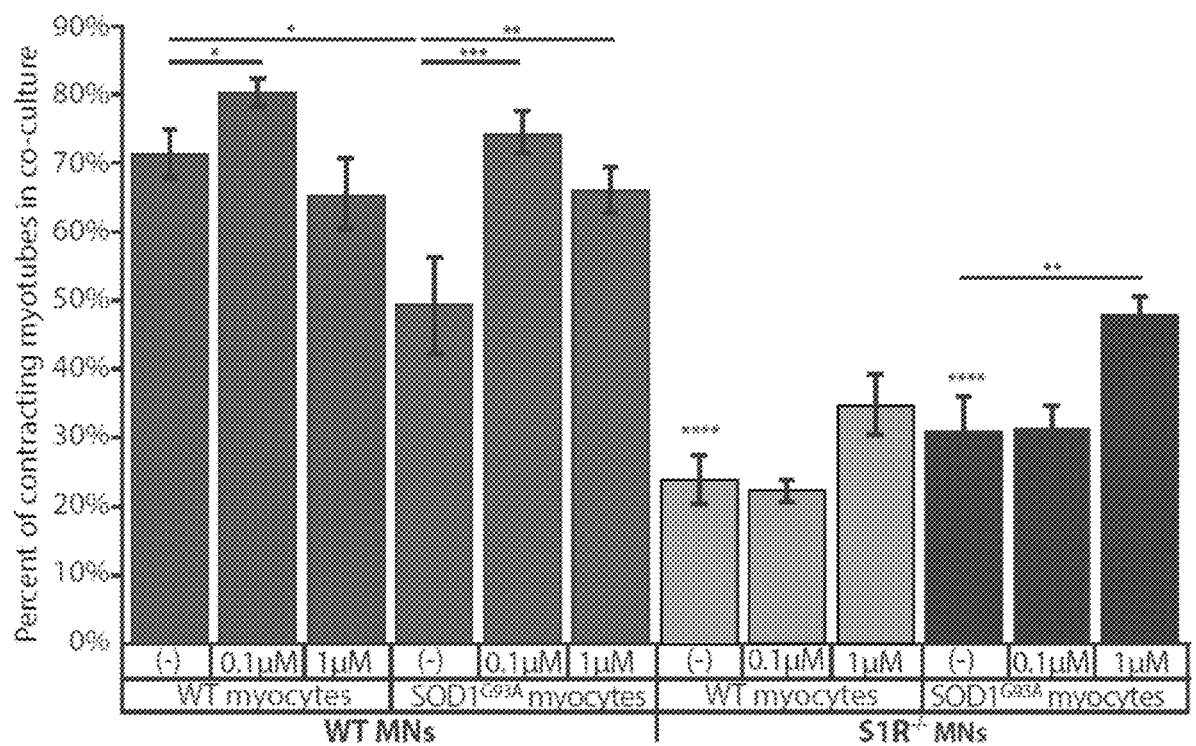

Quantification of the percentage of myofibers shows that in the absence of MNs, only ~10% of muscles contracted in the absence of MNs versus 74% in cultures including MNs. Co-culture combinations that include at least one of the cell types expressing SOD1G93A show a significantly lower percentage of contracting myocytes (FIG. 7a). Treatment of SOD1G93A myocytes co-cultured with pridopidine (0.1µM and 1µM) increases the percentage of contracting myocytes and restores neuromuscular activity to WT levels. Combination of S1R−/− MNs with WT myocytes results in a low number of contracting myotubes compared to WT MNs. Application of 0.1µM pridopidine to S1R−/− co-cultures did not restore the neuromuscular activity, as seen for the same concentration of pridopidine in co-cultures with WT neurons. The increase in the percentage of contracting myocytes observed after treatment with 1 µM pridopidine is significantly lower than the percentage of contracting myocytes in untreated and treated WT cultures. Data are shown as mean±SEM. *p-value<0.05; p-value<0.01, *p-value<0.001, ****p-value<0.0001. (Student's t-test).

Experiment 4: Activation of ERK in WT and SOD1G93A MNs

The ERK pathway promotes numerous cellular functions including proliferation and differentiation. ERK phosphorylation (activation) in neurons is associated with neurotrophic signaling, such as BDNF, which promotes neuroprotection and neuronal survival (Bonni 1999). It was previously established that pridopidine enhances BDNF signaling in rat striatum through S1R, which in turn, enhances ERK activation (Geva 2016). Primary MN cultures at 2 DIV were starved overnight in neurotrophin- and serum-free medium (PNB). The following day, cultures were treated for 30 minutes with pridopidine or with BDNF as a positive control.

Figure 8A:
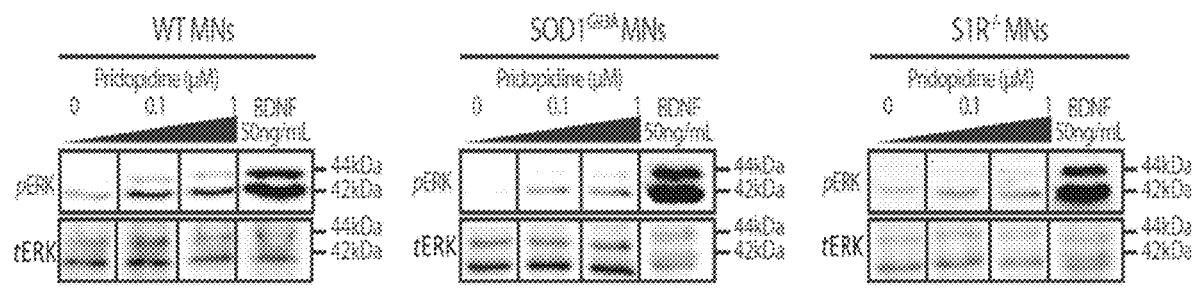
FIGS. 8a-8b. Effect of pridopidine on ERK levels.
Figure 8B:
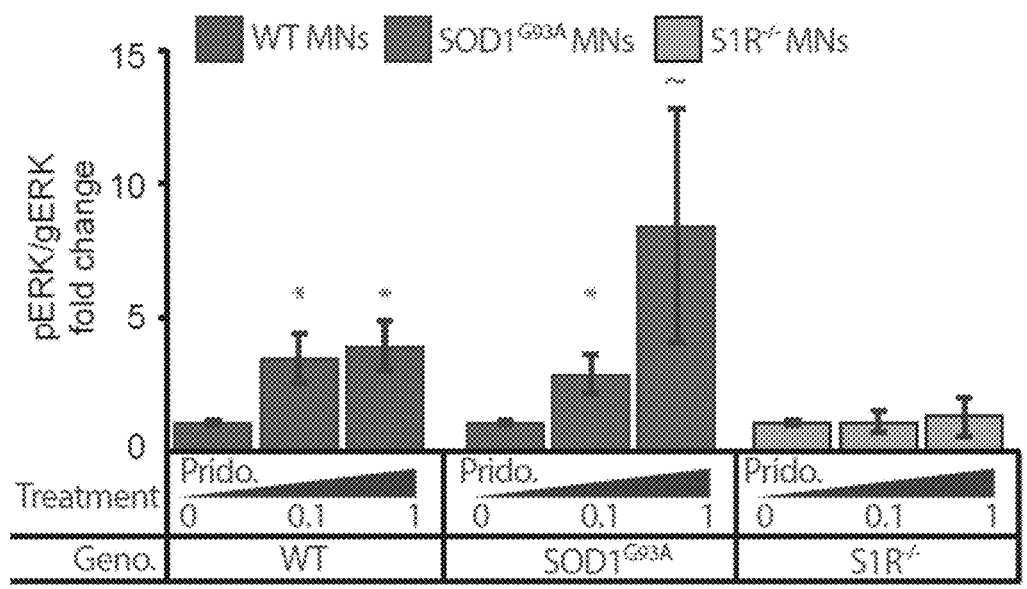

Results:

Western blot analyses for phosphorylated ERK (pERK) shows significant activation of ERK by pridopidine (0.1 µM and 1 µM), as early as 30 minutes after application in WT (left panel) and SOD1G93A (middle panel) MN cultures, but not in S1R−/− MN cultures (right panel) (FIG. 8a). Quantification of pERK reveals ~3.5 and ~4-fold increase in WT MNs following 0.1 µM and 1 µM pridopidine, respectively. SOD1G93A exhibits ~2.9 and ~8.5-fold increase in pERK following 0.1 µM and 1 µM pridopidine, respectively. Data are shown as the mean pERK/ERK ratios±SEM. *p-value<0.05, ~p-value<0.1 (Student's t-test) (FIG. 8b).

Experiment 5: Effect of Pridopidine on Mutant SOD1 Aggregates in the Spinal Cord of SOD1G93A Mice Pridopidine induced neuroprotective properties by activation of the S1R, as demonstrated for its effect on axonal transport, axonal degeneration, NMJ function and ERK activation. The S1R resides on the ER membrane in close proximity to the mitochondrial outer membrane, where the mutant SOD1 protein tends to aggregate in the spinal cord of SOD1G93A mice (Millecamps and Julien 2013). Presymptomatic SOD1G93A mice (5 weeks of age) and WT controls were treated with either saline, 3 or 30 mg/kg pridopidine, by daily s.c. (subcutaneous) administration for 11 weeks (until 16 weeks of age). At the end of the experiment, lumbar spinal cords (L1-L6) were extracted, fixed, and embedded for cryosectioning. Next, 10 µM sections were prepared and stained with NSC500 dye to visualize SOD1 aggregates (Hammarström 2010). The in vivo effect of pridopidine treatment on the number of mutant SOD1 aggregates in grey and white matter of spinal cord was evaluated.

Figure 9A:
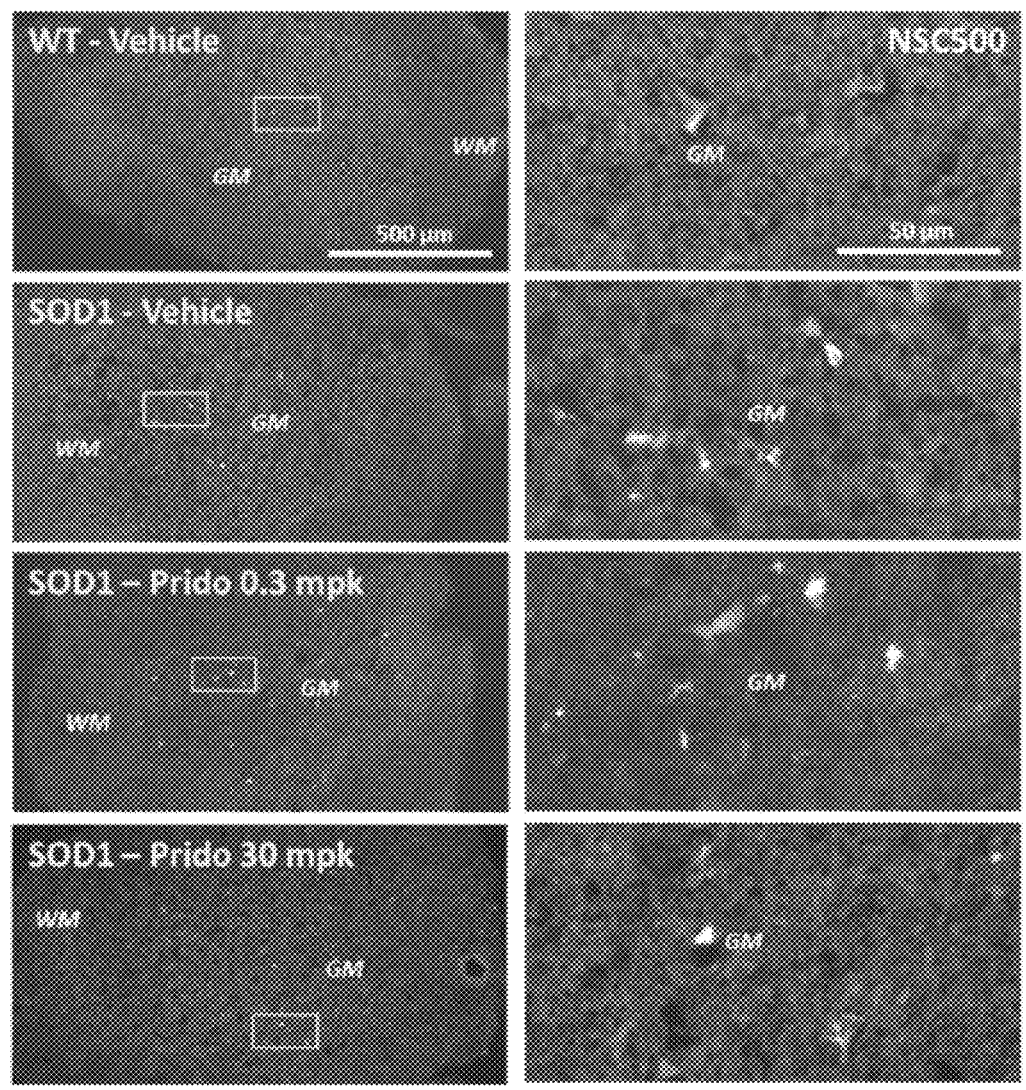
FIGS. 9a-9c. Effect of pridopidine on SOD1 aggregates.
Figure 9B:
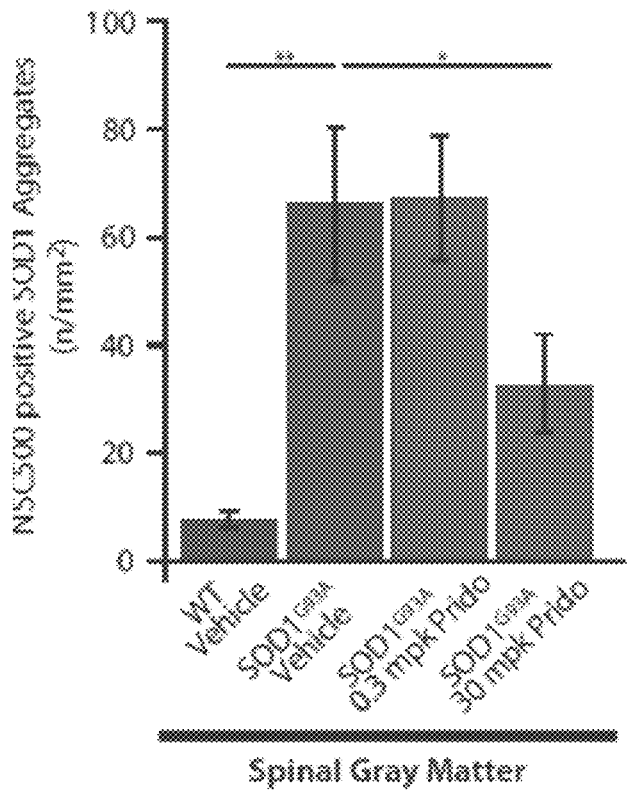
Figure 9C:
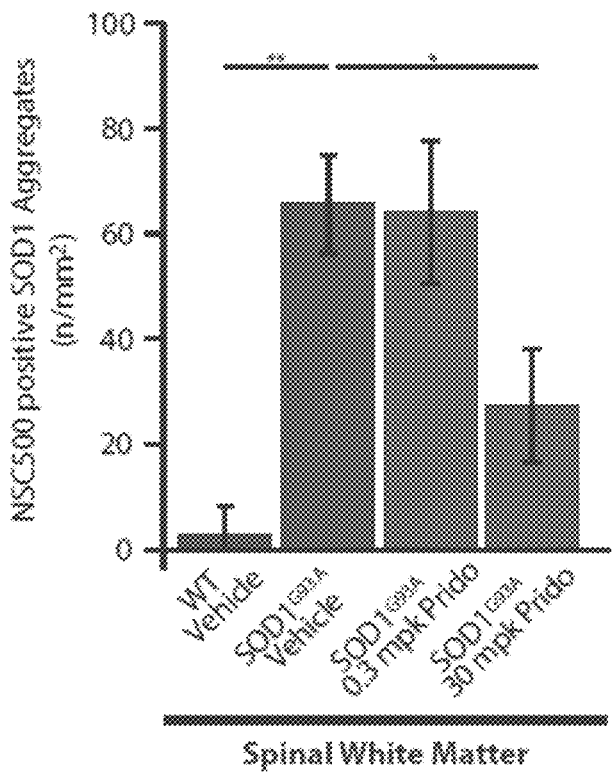

Results:

FIG. 9a-Left panel: low magnification representative images of fluorescently labeled spinal cords for 4 mouse groups. Right panel: high magnification images for the regions marked in the left panel by a square. Scale bars: Left panel: 500 µm; Right panel 50 µm. Top to bottom: WT vehicle, SOD1G93A vehicle, SOD1G93A 0.3 mg/kg pridopidine, SOD1G93A 30 mg/kg, all stained with NSC500 dye to label mutant SOD1 protein aggregates. A significant increase in the number of mSOD 1 aggregates was observed in both the gray and white matter of the spinal cords of SOD1G93A mice compared with WT mice. Pridopidine at 30 mg/kg significantly reduced the number of aggregates in both the gray and white matters of SOD1G93A spinal cords by ~50% (FIGS. 9a-9c). Data are shown as the mean±SEM. *p-value<0.05; **p-value<0.01 (one-way ANOVA followed by Fisher's LSD post hoc tests). (FIGS. 9b-9c y-axis is number of NSC500-positive SOD1 aggregates per squared mm).

Experiment 6: In-Vivo Evaluation of Muscle Fiber Atrophy and NMJ Preservation

Figure 10A:
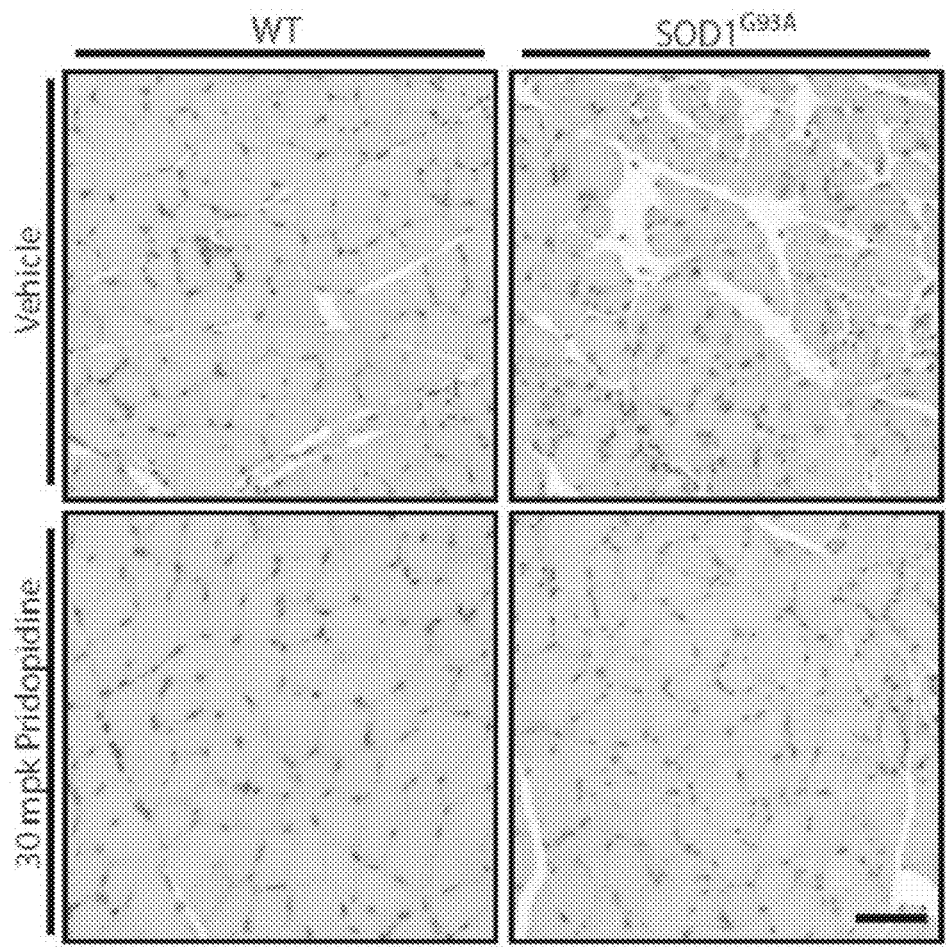
FIGS. 10a-10b. Effect of pridopidine on muscle tissue.

NMJ disruption and the subsequent skeletal muscle wasting are two main pathologies of ALS. Effect of pridopidine on muscle fiber atrophy and preservation of NMJs was evaluated in-vivo. Presymptomatic SOD1G93A mice and WT controls (5 weeks old) were treated with either saline, or pridopidine 3 or 30 mg/kg, by daily s.c. administration for 11 weeks. The Gastrocnemius muscles from vehicle or pridopidine-treated (30 mg/kg s.c.) mice were extracted from the SOD1G93A and WT mice at age 16 weeks. Muscle cross-sections were stained with Hematoxylin & Eosin (H&E), and the mean muscle fiber diameter was quantified for each group (FIG. 10a). NMJ preservation was evaluated by confocal imaging of co-localizing pre (NFH+Synapsin-I (green)- and post-synaptic (AchR (BTX; red) markers and counting the number of fully innervated NMJs in gastrocnemius muscles (FIG. 11a).

Figure 10B:
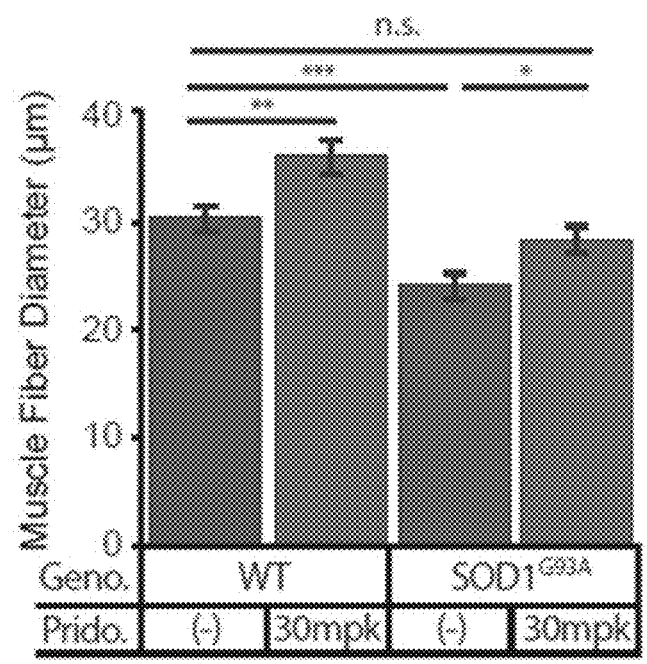

Results:

FIG. 10a: Representative images of H&E-stained cross-sections from Gastrocnemius muscle of mice from 4 groups: WT-vehicle treated, WT-30 mg/kg pridopidine treated. SOD1G93A-vehicle treated, and SOD1G93A-30 mg/kg pridopidine treated mice. Muscle histology of SOD1G93A-vehicle mice was poor and revealed a smaller diameter of muscle fiber as compared with WT-vehicle and WT-30 mg/kg pridopidine (FIGS. 10a-10b). Pridopidine (30 mg/kg, s.c. daily administration) led to a significant ~4 μm increase in the muscle fiber diameter in SOD1G93A and ~5 μm in WT muscles.

Figure 11A:
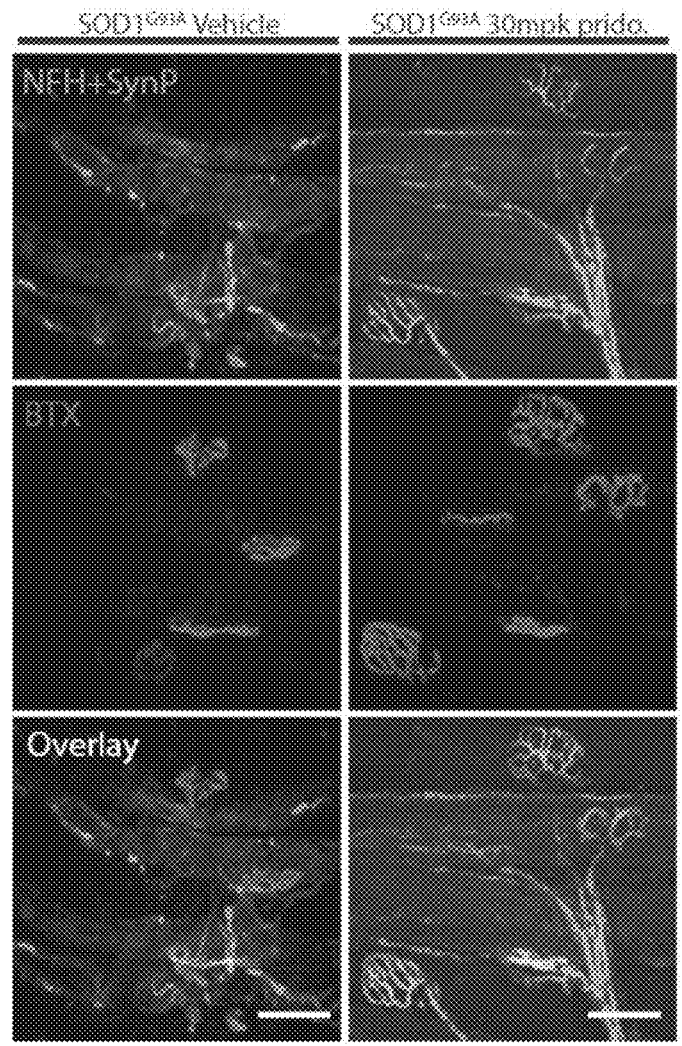
FIGS. 11a-11b. Effect of pridopidine on NMJ.
Figure 11B:
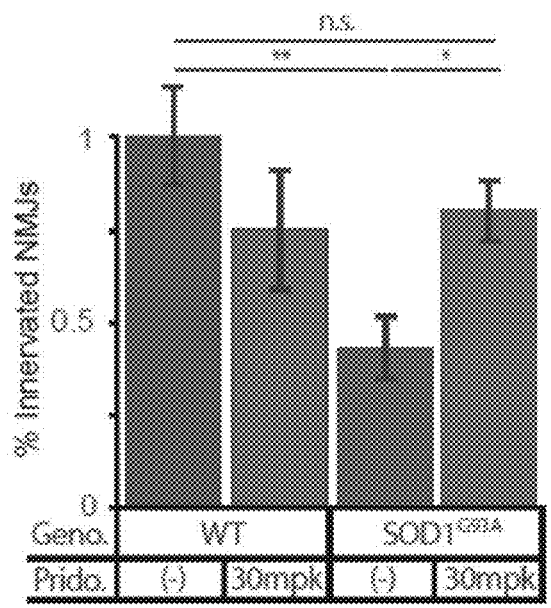

NMJ preservation in muscles of SOD1G93A vehicle-treated mice indicates the expected massive-60% loss of NMJ and morphological changes in the post-synaptic apparatus in the muscles of SOD1G93A mice compared to WT mice (FIGS. 11a-11b). Strikingly, Pridopidine treatment limited the loss of NMJs in SOD1G93A mice to ~20%. Data are shown as mean±SEM. *p-value<0.05; p-value<0.01; *p-value<0.001 (double-blind Student's t test).

Overall, these results demonstrate that pridopidine exerted neuroprotective effects in ALS cellular and animal models. In-vitro, in SOD1G93A MNs, pridopidine enhances BDNF axonal transport, upregulates ERK activation, enhances axonal growth, restores muscle innervation and improves NMJ formation and function. These neuroprotective effects were mediated by the S1R. In-vivo pridopidine treatment of SOD1G93A ALS mice reduced mutant SOD1 aggregation in spinal cord (one of the hallmark disease phenotype), increased the ALS-reduces muscle fiber diameter and preserved the degenerated NMJs observed in diseased tissue. These data support the use of pridopidine as neuroprotective agent and the S1R as a therapeutic target for the treatment of ALS patients.

Additional ALS animal models useful for testing pridopidine are described, for example, in McGoldrick (2013).

In the figures, abbreviations are as follows: Geno.=genotype (i.e. wild type (LM), mutant SOD1), Prido.=pridopidine, mpk=milligram per kilogram.

Experiment 7. Treatment of ALS in a Human Subject

Periodically orally administering of pridopidine provides a clinically meaningful advantage in reducing the symptoms of ALS in human subjects afflicted with ALS. Pridopidine therapy provides efficacy in treating the patient without undue adverse side effects and is effective in at least one of the following embodiments 1. The therapy is effective in improving symptoms of ALS:
2. The therapy is effective in enhancing BDNF axonal transport in motor neurons and/or enhancing ERK activation;
3. The therapy is effective in improving NMJ formation and preservation, preserving NMJ structure, preserving NMJ function and/or improving innervation rate of muscle tissue;
4. The therapy is effective in enhancing motor neuron axonal growth and/or reducing axonal degeneration, including motor neuron axonal degeneration;
5. The therapy is effective in enhancing muscle cell survival, enhancing muscle fiber diameter and function, reduce progression of muscle fiber wasting, and/or improve muscle contraction; and or
6. The therapy is effective in reducing SOD1 aggregation and/or lessening pseudobulbar disease progression.

In some patients, the attending physician administers pridopidine and a second compound, wherein the second compound is second compound is riluzole, edaravone, dextromethorphan/quinidine. In some embodiments, the second compound is laquinimod.

REFERENCES

Banci et al. (2008) SOD1 and Amyotrophic Lateral Sclerosis: Mutations and Oligomerization, PLoS One 3(2): e1677.

Bilsland et al. (2010) Deficits in axonal transport precede ALS symptoms in vivo. Proc Natl Acad Sci USA. 107 (47):20523-8.

Bonni A, et al. (1999) Cell survival promoted by the Ras-MAPK signaling pathway by transcription-dependent and -independent mechanisms. Science 286:1358-1362

Bozzoni et al. (2016) Amyotrophic lateral sclerosis and environmental factors", Funct. Neurol. 31(1):7-19.

Brod et al. (2000) Combination therapy with glatiramer acetate (copolymer-1) and a type I interferon (IFN-α) does not improve experimental autoimmune encephalomyelitis. Annals of Neurology, 47:127-131.

Cedarbaum (1999) The ALSFRS-R a revised ALS functional rating scale that incorporates assessments of respiratory function. J. Neurol. Sci. 169(1-2):13-21.

De Vos et al. (2007) Familial amyotrophic lateral sclerosis-linked SOD1 mutants perturb fast axonal transport to reduce axonal mitochondria content. Hum Mol Genet. 16(22):2720-2728.

Eykens C, Robberecht W (2015) The genetic basis of amyotrophic lateral sclerosis: recent breakthroughs. Adv Genomics Genetics 5:327-345.

Geva et al. (2016). Pridopidine activates neuroprotective pathways impaired in Huntington Disease. HMG 25(18): 3975-87.

Guidance for Industry. In vivo drug metabolism/drug interaction studies—study design, data analysis, and recommendations for dosing and labeling, U.S. Dept. Health and Human Svcs., FDA, Ctr. for Drug Eval. and Res., Ctr. For Biologics Eval. and Res., Clin. Pharm., November 1999 <http://www.fda.gov/cber/gdlns/metabol.pdf>.

Hammarström P, et al, (2010) A fluorescent pentameric thiophene derivative detects in vitro-formed prefibrillar protein aggregates. Biochemistry 49:6838-45

Ionescu et al. (2016) Compartmental microfluidic system for studying muscle-neuron communication and neuromuscular junction maintenance. (2016) European Journal of Cell Biology 95(2) 69-88.

Langa F et al. (2003) Generation and phenotypic analysis of sigma receptor type 1 (sigma 1) knockout mice. Eur J Neurosci. 18:2188-96.

Maier et al. (2013) Differentiated NSC-34 motorneuron-like cells as experimental model for cholinergic neurodegeneration, Neurochem. Int. 62(8): 1029-38.

Martel et al. (2016) From animal models to human disease: a genetic approach for personalized medicine in ALS, Acta Neuropathol. Commun. 4(1):70.

McGoldrick et al. (2013) Rodent models of amyotrophic lateral sclerosis. BBA Mol. Basis of Disease 1832 (9): 1421-1436.

Millecamps and Julien (2013) Axonal transport deficits and neurodegenerative diseases. Nat Rev Neurosci. 14:161-76.

Perlson, et al. (2009) A Switch in Retrograde Signaling from Survival to Stress in Rapid Onset Neurodegeneration. J Neurosci. 2009 29(31): 9903-9917.

Peters et al. (2015) Emerging mechanisms of molecular pathology in ALS, J. Clin. Invest. 125(5): 1767-1779.

Ponten, et al. (2010). In vivo pharmacology of the dopaminergic stabilizer pridopidine. Eur J Pharmacol. 644(1-3): 88-95.

Riva et al. (2016) Recent advances in amyotrophic lateral sclerosis, J. Neurol. 263:1241-1254.

Ryskamp, et al (2017) The sigma-1 receptor mediates the beneficial effects of pridopidine in a mouse model of Huntington disease. Neurobiol of Disease 97(Pt A):46-59.

Sahlholm et al. (2013) The dopamine stabilizers ACR16 and (−)-OSU6162 display nanomolar affinities at the s-1 receptor. Molec Psychiatry 18, 12-14.

Sahlholm et al. (2015) Pridopidine selectively occupies sigma-1 rather than dopamine D2 receptors at behaviorally active doses. Psychopharm. 232(18):3342-53.

Smith, et al. (2017). Enhanced Bulbar Function in Amyotrophic Lateral Sclerosis: The Nuedexta Treatment Trial. Neurotherapeutics, 14(3), 762-772.

Song et al. (2013) An update on amine oxidase inhibitors: Multifaceted drugs, Prog. Neuropyschopharmacol. Biol. Psychiatry 44:118-124.

Zou et al. (2016) Toward precision medicine in amyotrophic lateral sclerosis, Ann. Transl. Med. 4(2):27.

Zahavi, et al. (2015) A compartmentalized microfluidic neuromuscular co-culture system reveals spatial aspects of GDNF functions. J. Cell Sci. 128, 1241-1252.

Riluzole—Drug Summary, PDR (Prescribers' Digital Reference), www.pdr.net/drug-summary/Rilutek-riluzole-526 accessed Jul. 28, 2017

Edaravone—Drug Summary, PDR (Prescribers' Digital Reference), www.pdr.net/drug-summary/Radicava-edaravone-24080 accessed Jul. 28, 2017

Dextromethorphan hydrobromide/quinidine sulfate—Drug Summary, PDR (Prescribers' Digital Reference), http://www.pdr.net/drug-summary/Nuedexta-dextromethorphan-hydrbromide-quinidine-sulfate-1344.3281 accessed Aug. 14, 2017

U.S. Pat. No. 7,923,459

U.S. Pat. No. RE46117

PCT Application Publication No. WO 2016/138135

PCT Application Publication No. WO 2017/015609

What is claimed is:

1. A method for treating a subject afflicted with sporadic amyotrophic lateral sclerosis (ALS), comprising periodically administering to the subject an amount of pridopidine or a pharmaceutically acceptable salt thereof effective to treat the subject.

2. The method of claim 1, wherein the amount of pridopidine is effective to inhibit or reduce progression of a symptom of the sporadic ALS in the subject.

3. The method of claim 2, where in the symptom is muscles stiffness, muscle weakness, muscle wasting, muscle cramps, difficulty speaking, difficulty swallowing, difficulty breathing, difficulty chewing, difficulty walking, fasciculations, and/or worsening posture.

4. The method of claim 1, wherein the amount of pridopidine is effective to enhance BDNF axonal transport in motor neurons, enhance ERK activation in motor neurons, improve NMJ formation and preservation, preserve NMJ structure, preserve NMJ function, improve innervation rate of muscle tissue, enhance motor neuron axonal growth, reduce axonal degeneration, reduce motor neuron axonal degeneration, enhance muscle cell survival, enhance muscle fiber diameter and function, reduce SOD1 aggregation, lessen pseudobulbar disease progression, reduce progression of muscle fiber wasting, and/or improve muscle contraction in the subject afflicted with ALS.

5. The method of claim 1, wherein the amount of pridopidine is administered daily, twice a week, three times a week or more often than once daily.

6. The method of claim 1, wherein the amount of pridopidine is administered twice daily.

7. The method of claim 1, wherein the amount of pridopidine is administered orally.

8. The method of claim 1, wherein the amount of pridopidine administered is 10 mg per day to 90 mg per day.

9. The method of claim 1, wherein the pridopidine is pridopidine hydrochloride.

10. The method of claim 1, wherein the subject is a human subject.

11. The method of claim 1, further comprising administering to the subject a therapeutically effective amount of a second compound, wherein the second compound is riluzole, edaravone, dextromethorphan/quinidine, sodium phenylbutyrate (PB), tauroursodeoxycholic acid or sodium phenylbutyrate (PB)/tauroursodeoxycholic acid.

12. The method of claim 11, wherein the administration of the second compound precedes the administration of pridopidine.

13. The method of claim 11, wherein the administration of pridopidine precedes the administration of the second compound.

14. The method of claim 11, wherein the pridopidine is administered adjunctively to the second compound.

15. The method of claim 11, wherein the second compound is administered adjunctively to the pridopidine.

* * * * *